(12) United States Patent
Chen

(10) Patent No.: US 11,837,659 B2
(45) Date of Patent: Dec. 5, 2023

(54) INTEGRATED CIRCUIT WITH DRAIN WELL HAVING MULTIPLE ZONES

(71) Applicants: TAIWAN SEMICONDUCTOR MANUFACTURING COMPANY, LTD., Hsinchu (TW); TSMC CHINA COMPANY, LIMITED, Songjiang (CN)

(72) Inventor: Zheng Long Chen, Hsinchu (TW)

(73) Assignees: TAIWAN SEMICONDUCTOR MANUFACTURING CO., LTD., Hsinchu (TW); TSMC CHINA COMPANY, LIMITED, Shanghai (CN)

( * ) Notice: Subject to any disclaimer, the term of this patent is extended or adjusted under 35 U.S.C. 154(b) by 95 days.

(21) Appl. No.: 17/165,126

(22) Filed: Feb. 2, 2021

(65) Prior Publication Data

US 2022/0115536 A1 Apr. 14, 2022

(30) Foreign Application Priority Data

Oct. 12, 2020 (CN) .......................... 202011082905.X

(51) Int. Cl.
*H01L 29/78* (2006.01)
*H01L 29/66* (2006.01)

(52) U.S. Cl.
CPC .... *H01L 29/7833* (2013.01); *H01L 29/66553* (2013.01); *H01L 29/66689* (2013.01); *H01L 29/7817* (2013.01)

(58) Field of Classification Search
CPC ........... H01L 29/7833; H01L 29/66553; H01L 29/66689; H01L 29/7817; H01L 29/665; H01L 29/66659; H01L 21/26586; H01L 29/456; H01L 29/0847; H01L 29/7835; H01L 29/7816; H01L 29/0607; H01L 29/0878; H01L 29/0882; H01L 29/36; H01L 29/66681
See application file for complete search history.

(56) References Cited

U.S. PATENT DOCUMENTS

| | | | |
|---|---|---|---|
| 6,734,493 B2 | 5/2004 | Chen et al. |
| 7,829,408 B2 | 11/2010 | Lin et al. |
| 8,138,049 B2 | 3/2012 | You |
| 8,692,327 B2 | 4/2014 | Ko et al. |

(Continued)

OTHER PUBLICATIONS

Cai, Jun, et al. "A novel high performance stacked LDD RF LDMOSFET." IEEE Electron Device Letters 22.5 (2001): 236-238. (pp. 1-3).

(Continued)

*Primary Examiner* — Mohammed R Alam
(74) *Attorney, Agent, or Firm* — Hauptman Ham, LLP

(57) ABSTRACT

An integrated circuit includes a drift region in a substrate, a drain in the substrate which includes a doped drain well, the doped drain well including a first zone, having a first concentration of a first dopant, and a second zone, having a second concentration of the first dopant, where the first concentration is smaller than the second concentration, and a gate electrode over the drift region and being separated from the doped drain well in a direction parallel to a top surface of the substrate by a distance greater than 0.

20 Claims, 20 Drawing Sheets

(56) References Cited

U.S. PATENT DOCUMENTS

2016/0043216 A1* 2/2016 He .................. H01L 29/0873
257/328
2018/0190816 A1* 7/2018 Siddiqui ........... H01L 29/66659
2020/0335623 A1* 10/2020 Shin ................. H01L 29/7816

OTHER PUBLICATIONS

Office Action dated Jun. 21, 2022 for corresponding case No. TW 11120603670. (pp. 1-7).

* cited by examiner

INTEGRATED CIRCUIT WITH DRAIN WELL HAVING MULTIPLE ZONES

BACKGROUND

A laterally-diffused metal-on-silicon (LDMOS) is a planar field effect transistor used for power amplification in integrated circuits. Manufacturing techniques for LDMOS devices include multiple implant processes into P-type silicon substrates or P-type epitaxial layers. Power amplifiers boost low power signals to have a higher power and drive devices such as antennas.

DETAILED DESCRIPTION

Figure 1:
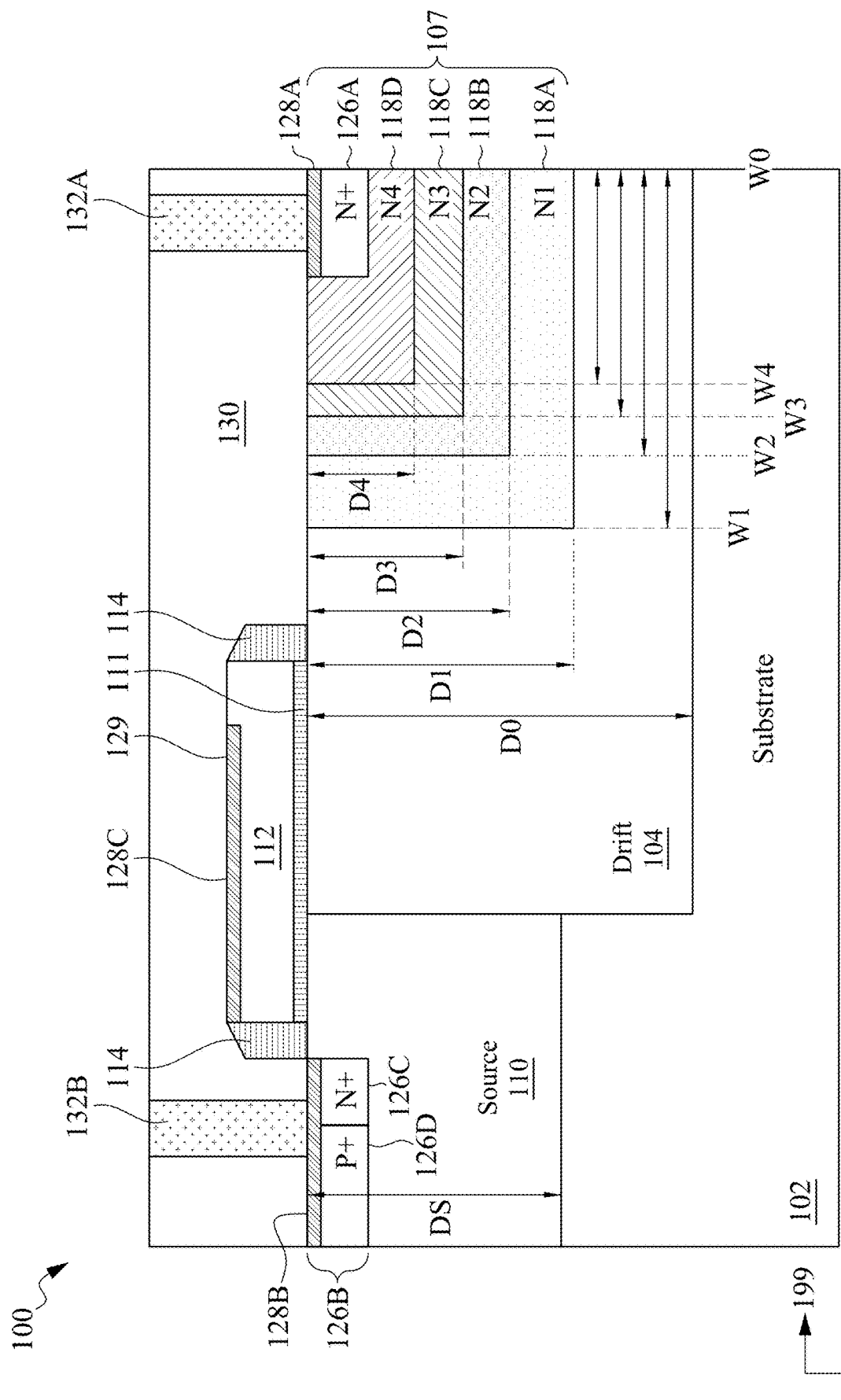
FIG. 1 is a cross-sectional view of a laterally-diffused metal-on-silicon (LDMOS), in accordance with some embodiments.

The following disclosure provides many different embodiments, or examples, for implementing different features of the provided subject matter. Specific examples of components, values, operations, materials, arrangements, etc., are described below to simplify the present disclosure. These are, of course, merely examples and are not intended to be limiting. Other components, values, operations, materials, arrangements, or the like, are contemplated. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

Laterally-diffused metal-oxide semiconductor (LDMOS) devices are transistors having dopants in a substrate that form source wells, drain wells, and drift regions suitable for use in power amplifiers and the like. LDMOS devices and bipolar junction transistors (BJT devices) have high breakdown voltages and operate over a wide range of voltages with fast switching times and large current flows. An LDMOS device is an asymmetric power metal-oxide semiconductor field effect transistor (MOSFET) with lower on-resistance and higher blocking voltages than other MOSFETs. The current between the source well and drain well of an LDMOS is controlled by the electrical field induced (by the gate electrode) in the drift region of a substrate between the source well and the drain well of the LDMOS device. The current of an LDMOS device is predominantly lateral parallel to the top surface of the substrate between the source well and the drain well of the device. LDMOS devices are made as either P-type MOSFETs or as N-type MOSFETs.

In semiconductor devices such as LDMOS devices which are designed to carry large currents, the base or drain sometimes experiences a phenomenon called the Kirk effect. The Kirk effect occurs when the base/drain undergoes "base pushout," the expansion of the base width with the flow of high current (e.g., a high concentration of carriers) moving between the drain and source (for, e.g., an LDMOS device). In an LDMOS device, base pushout arises when the density of the minority carriers injected into the drain depletion region becomes comparable to the doping level in the drain. The large number of carriers compensates for ions in the depletion region, reducing the electric field between the source and drain. When the charge density of carriers matches or exceeds the charge density in the depletion zone of the drain well, the depletion zone disappears and the transit time of carriers across the length of the channel increases, reducing the overall switching speed of the LDMOS device.

Reducing the channel length, which occurs in subsequent generations of semiconductor devices in order to decrease the switching time of the devices, tends to make the devices more prone to base pushout, and to decrease the breakdown voltage of the devices during operation. In order to increase the breakdown voltage of the LDMOS, the gate poly-silicon of the LDMOS is extended over the drift region of the LDMOS. An overlapped gate electrode functions as a field plate to maintain the breakdown voltage of the LDMOS.

In LDMOS devices with a drain well having a single concentration zone of dopant, shrinking the dimensions of the device results in faster switching time and lower breakdown voltages. By increasing the number of concentration zones of dopant in the drain well of an LDMOS, a smaller channel length is maintained with a breakdown voltage comparable to an LDMOS device with a single concentration zone of dopant in the drain well. Further, increasing the number of concentration zones of dopant in the drain well improves the LDMOS device's resistance to the Kirk effect. In some embodiments, a drain well with multiple concentration zones of dopant is able to withstand greater current without carrier saturation increasing the carrier transit time across the channel. Further, base pushout reaching a first, low concentration zone of dopant in the drain well, does not achieve the carrier density to saturate a second, higher concentration zone of dopant in the drain well. Furthermore, by increasing the separation between the concentration zones of dopant in the drain well at the top surface of the substrate, the breakdown voltage is also increased. Examples of LDMOS devices having multiple concentration zones (zones) of dopant in the drain well are described below, as well as a method of making LDMOS devices having drain wells with multiple zones therein.

FIG. 1 is a cross-sectional view of an integrated circuit 100, in accordance with some embodiments. In FIG. 1, a substrate 102 includes a drift region 104, a source well 110, and a drain well 107. In some embodiments, substrate 102 is a P-type substrate containing silicon and a P-type dopant such as boron. Source well 110 is a P-doped well, drain well 107 is an N-doped well, and the drift region 104 includes a net concentration of N-type dopants. In some embodiments, the source well is an N-doped well, the drain well is a P-doped well, and the drift-region includes a net concentration of P-type dopants. One of ordinary skill in the art would understand that other configurations are also within the scope of the present disclosure including the use of different dopant types.

Drain well 107 includes a first doped zone 118A (N1), a second doped zone 118B (N2), a third doped zone 118C (N3), and a fourth doped zone 118D (N4). First doped zone 118A separates second doped zone 118B from drift region 104. Second doped zone 118B separates third doped zone 118C from first doped zone 118A. Third doped zone 118C separates fourth doped zone 118D from second doped zone 118B. Fourth doped zone 118D separates drain LDD region 126A from third doped zone 118C.

First doped zone 118A has a smallest concentration of dopant atoms of the doped zones of drain well 107. Drift region 104 has a concentration of dopant (same type of dopant in the drain well 107) which is smaller than the dopant concentration in first doped zone 118A. Fourth doped zone 118D has a highest concentration of dopant atoms in the zones of drain well 107. Second doped zone 118B and third doped zone 118C have dopant concentrations between the concentration in first doped zone 118A and fourth doped zone 118D. Second doped zone 118B has a dopant concentration greater than the dopant concentration in first doped zone 118A, and smaller than the dopant concentration in third doped zone 118C.

Drift region 104 extends below the top surface of the substrate 102 by a drift region depth D0. Depth D0, and other depths described hereinafter, are measured parallel to a first direction 198 extending perpendicular to the top surface of substrate 102. A second direction 199 extends perpendicular to the first direction 198. Second direction 199 extends parallel to the top surface of substrate 102, along a shortest distance from the drain well 107 to the source well 110 under gate dielectric 111. First doped zone 118A has first zone depth D1 below the top surface of the substrate 102, second doped zone 118B has a second zone depth D2 below the top surface of the substrate 102, third doped zone 118C has a third zone depth D3 below the top surface of the substrate 102, and fourth doped zone 118D has a fourth zone depth D4 below the top surface of the substrate. In integrated circuit 100, D0>D1>D2>D3>D4. In some embodiments, D0>D1=D2>D3>D4. In some embodiments, D0>D1>D2=D3>D4. In some embodiments, D0>D1>D2>D3=D4. In some embodiments, D0>D1=D2>D3=D4. In some embodiments, D0>D1=D2=D3>D4. In some embodiments, D0>D1>D2=D3=D4. In some embodiments, D0>D1=D2=D3>D4. In some embodiments, D0>D1>D2=D3=D4. In some embodiments, D0>D1=D2=D3=D4. In some embodiments, one or more of the doped zones have a zone depth equal to the drift region depth D0 (e.g., D0=D1=D2=D3=D4).

In some embodiments, first zone depth D1 ranges from 20% of the doped region depth D0 to 100% of doped region depth D0 (e.g., $D0 \geq D1 \geq (0.2) \times D0$). In some embodiments, second zone depth 118B (D2) ranges from 20% of doped region depth D0 to 100% of doped region depth D0 (e.g., $D0 \geq D2 \geq (0.2) \times D0$). In some embodiments, third zone depth 118C (D3) ranges from 20% of doped region depth D0 to 100% of doped region depth D0 (e.g., $D0 \geq D3 \geq (0.2) \times D0$). In some embodiments, fourth zone depth 118D (D4) ranges from 20% of doped region depth D0 to 100% of doped region depth D0 (e.g., $D0 \geq D4 \geq (0.2) \times D0$). In some embodiments, the zone depths of doped zones in the drain well not less than the depth of the LDD region (see, e.g., drain LDD region 126A) in a drain well. In some embodiments, depth ratios between D0, D1, D2, D3, and D4 are different from the above examples.

Doped zones 118A-118D have doped zone widths measured from the edge (W0) of the drain well farthest from the gate electrode 112 to the edge of the doped zone closest to the gate electrode 112 along the second direction 199. First doped zone 118A has a first zone width W1. Second doped zone 118B has a second zone width W2, smaller than first zone width W1. Third doped zone 118C has a third zone width W3 smaller than second zone width W2. Fourth doped zone 118D has a fourth zone width W4 smaller than the third zone width (e.g., W1>W2>W3>W4). In some embodiments, widths W1-W4 are different from the above examples.

In some embodiments, the first zone width W1 is the same as the second zone width W2 (see, e.g., FIG. 5B-5C, below) at the top surface of the substrate. In some embodiments, the first zone width W1 is larger than the second zone width W2 (see, e.g., FIGS. 5D-5E, below) at the top surface of the substrate. In some embodiments, the third zone width W3 is the same as the fourth zone width W4 at the top of the substrate (see, e.g., FIG. 5C, below). In some embodiments, the third zone width W3 is larger than fourth zone width W4 (see FIGS. 5D-5E, below).

Figure 5A:
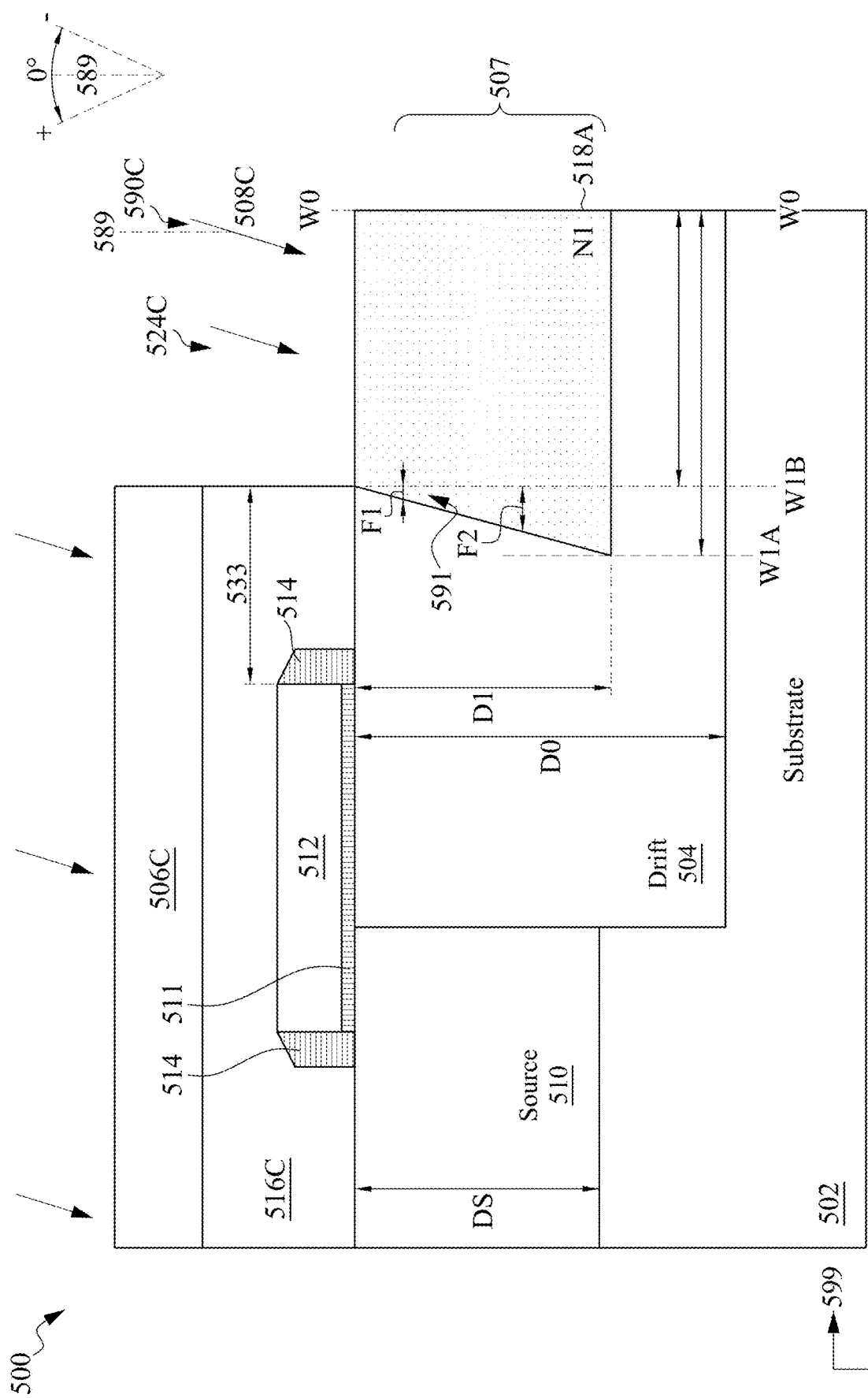
FIGS. 5A-5E are cross-sectional views of a LDMOS during a manufacturing process, in accordance with some embodiments.
Figure 5B:
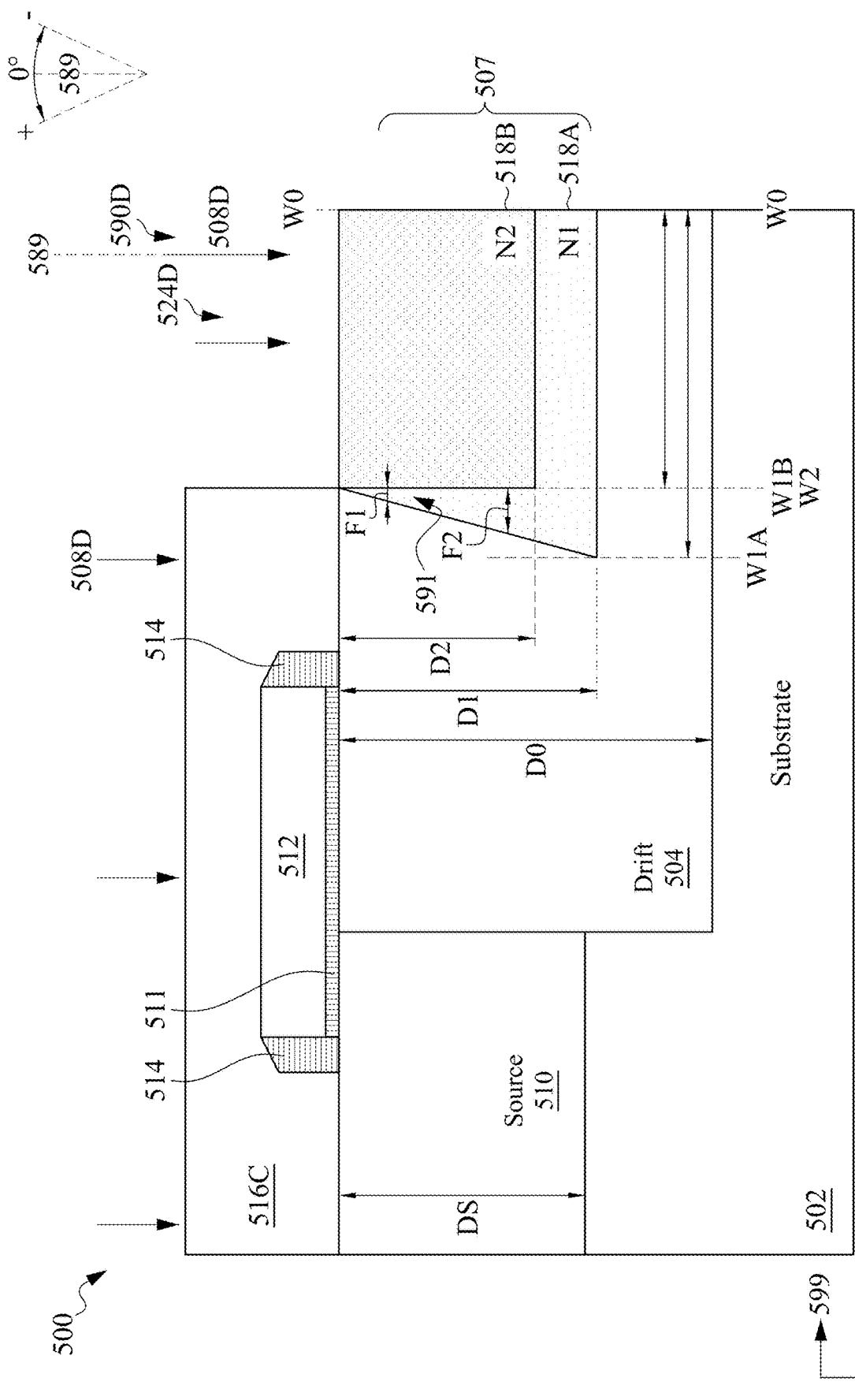
Figure 5C:
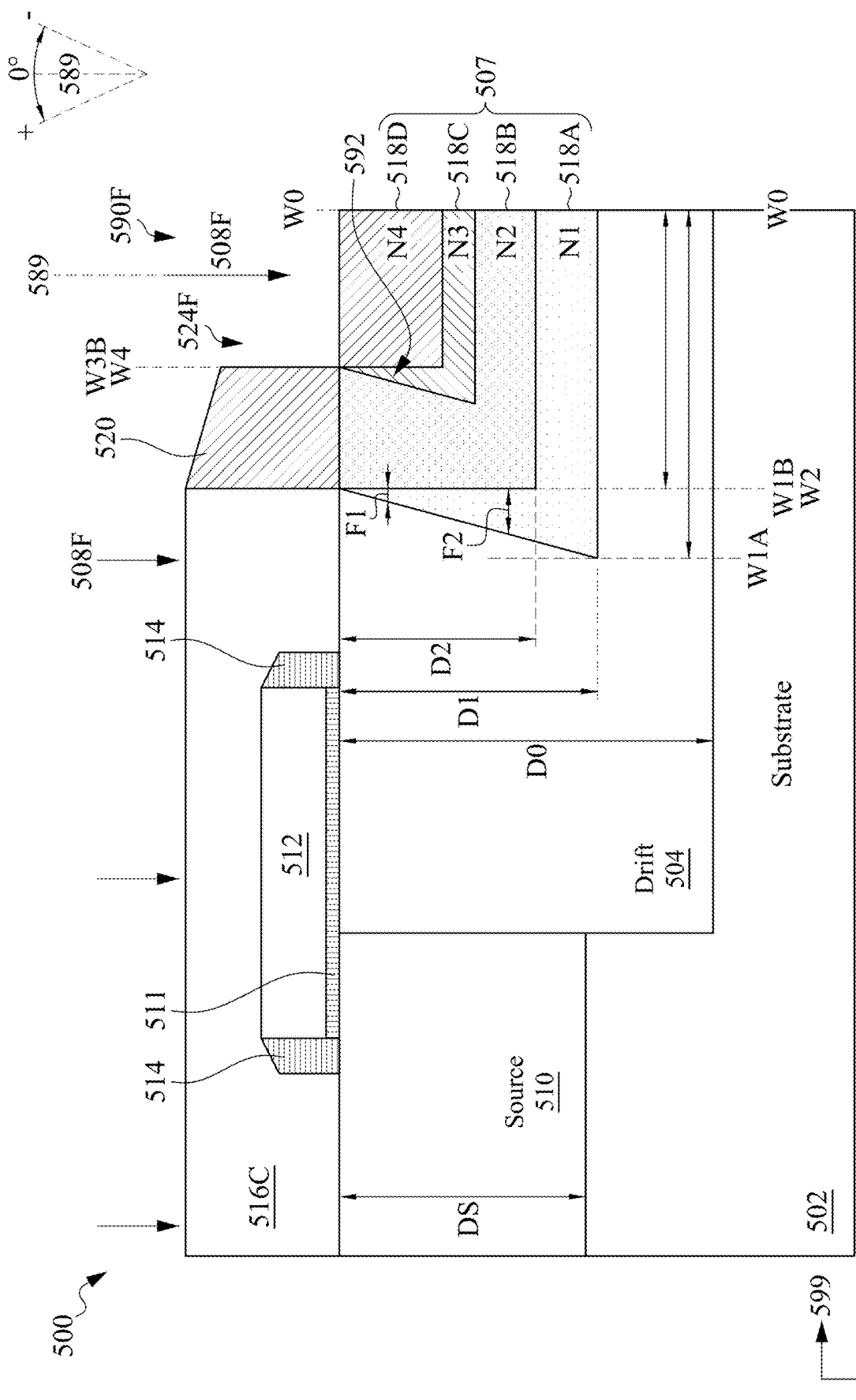
Figure 5D:
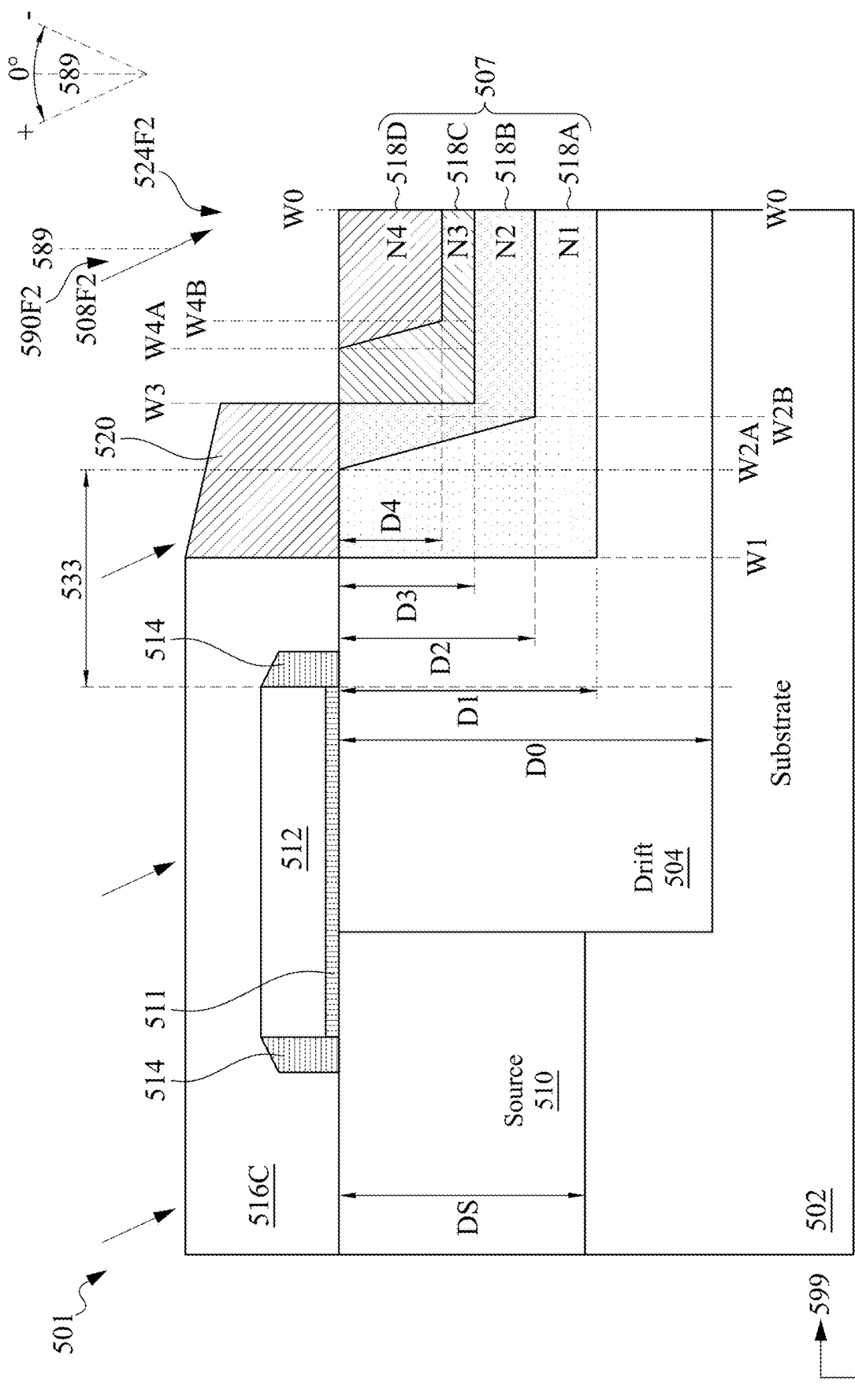

For embodiments similar to the drain well 507 in FIG. 5D: In some embodiments, the first zone width W1 is wider than the width of the top of the second doped zone W2B, or the width of the bottom of the second zone W2A. In some embodiments, the width of the top of the second doped zone W2B and the width of the bottom of the second zone W2A are both wider than the third zone width W3. In some embodiments, the third zone width W3 is larger than the width of the top of the fourth doped zone W4B, and the width of the bottom of the fourth zone W4A.

Figure 5E:
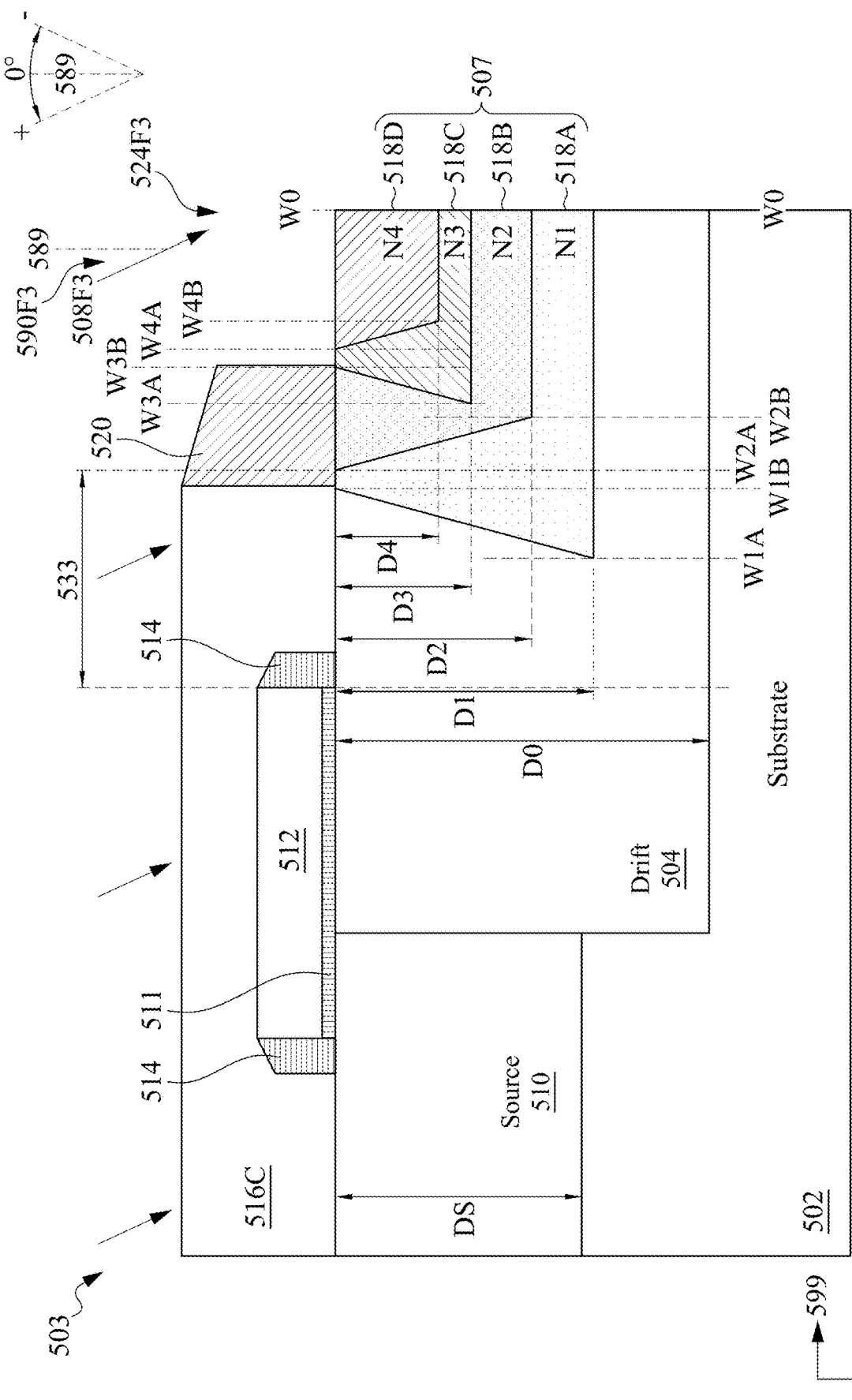

For embodiments, similar to the drain well 507 in FIG. 5E: In some embodiments, the first zone top width W1B and the first zone bottom width W1A are both larger than the second zone top width W2B and second zone bottom width W2A. In some embodiments, the second zone top width W2B and the second zone bottom width W2A are both larger than the third zone top width W3B and third zone bottom width W3A. In some embodiments, the third zone top width W3B and the third zone bottom width W3A are both larger than the fourth zone top width W4B and fourth zone bottom width W4A.

Drain LDD region 126A is located at a top surface of drain well 107 and within fourth doped zone 118D. Drain LDD region 126A has a same type of dopant as the doped zones 118A-118D of drain well 107, and a concentration of dopants greater than the concentration of dopants in the drift region 104 or any of doped zones 118A-118D. Drain LDD region 126A has a drain LDD silicide 128A at the top surface thereof, and directly against contact 132A.

Drift region 104 is against source well 110 and separates source well 110 from drain well 107. The doped zones 118A-118D in drain well 107 are separated from source well 110 by the drift region 104. In embodiments of LDMOS devices having smaller or larger numbers of doped zones in the drain well, the drift region separates the doped zones from the source well.

Source well 110 is against the top surface of the substrate 102 and against the drift region 104. Source well 110 includes source LDD region 126B, which comprises N-doped source LDD zone 126C and P-doped source LDD zone 126D. N-doped source LDD zone 126C is directly against P-doped source LDD zone 126D at the top surface of source well 110 in substrate 102, with N-doped source LDD zone 126C closer to gate electrode 112 than P-doped source LDD zone 126D. Source LDD region 126B is topped by a source LDD silicide 128B which extends across N-doped source LDD zone 126C and P-doped source LDD zone 126D. Source LDD silicide 128B is directly against contact 132B.

Gate dielectric 111 is against the top surface of drift region 104 and the top surface of source well 110, and separated from the source LDD region 126B (or, separated from N-doped source LDD zone 126C) by spacer 114. Spacer 114 is on both the source-well side of gate electrode 112 and gate dielectric 111, and the drain-well side of gate electrode 112 and gate dielectric 111. An interface between the gate electrode 112 and the spacer 114 on the drain-well side of gate electrode 112 is a gate separation distance 129 from the inner edge (e.g., the edge closer to the gate electrode, or to the interface between drift region 104 and source well 110) of first doped zone 118A. The gate separation distance 129 correlates approximately linearly with the breakdown voltage of the device. A gate electrode silicide 128C covers part of the top surface of gate electrode 112. A portion of the top surface of gate electrode 112, on the drain-well side of the gate electrode, is exposed gate electrode material and not gate electrode silicide.

Inter layer dielectric (ILD) 130 extends over the top surface of the drain LDD silicide 128A, drain well 107, drift region 104, spacer 114, gate electrode 112, gate electrode silicide 128C, and source LDD silicide 128B. ILD layer 130 is a layer of dielectric material deposited by, e.g., a form of chemical vapor deposition (CVD), to electrically isolate source well 110 (or, source LDD region 126B and source LDD silicide 128B and contact 132B) from gate electrode 112 and gate electrode silicide 128C, and a gate electrode contact (not shown), and drain well 107, drain LDD region 126A, drain LDD silicide 128A, and contact 132A. Contact 132A extends entirely through ILD 130 to electrically connect to drain LDD silicide 128A, and contact 132B extends entirely through ILD 130 to electrically connect to source LDD silicide 128B.

Figure 2:
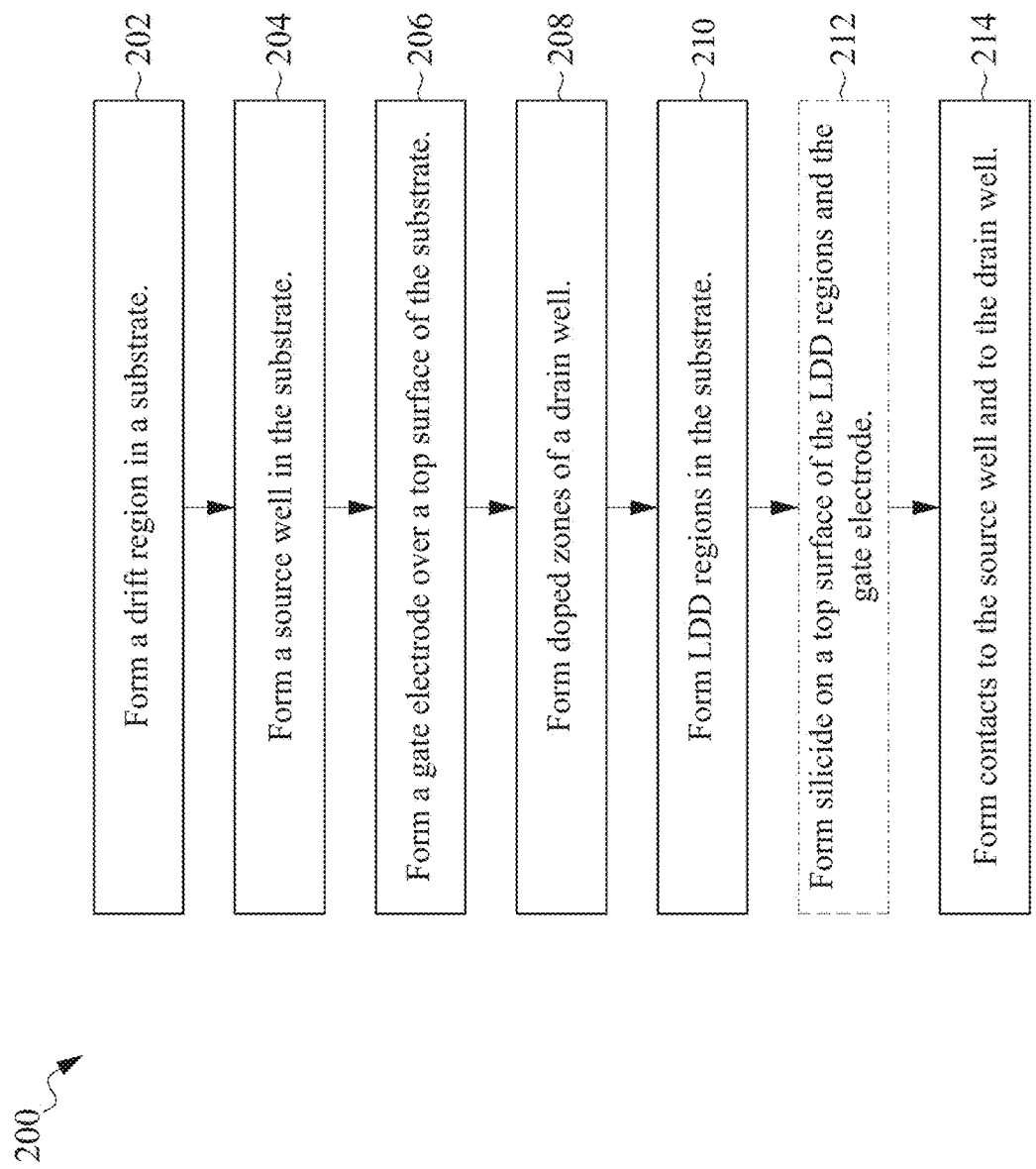
FIG. 2 is a flow diagram of a method of making a LDMOS, in accordance with some embodiments.

FIG. 2 is a flow diagram of a method 200 of making a LDMOS, in accordance with some embodiments.

Method 200 includes an operation 202, wherein a drift region is formed in a substrate. In the making of a drift region in a substrate, operation 202 includes steps directed toward covering the substrate, such as a substrate which comprises a P-doped semiconductor material, with a layer of patterning material. Operation 202 includes steps directed toward performing a doping process to create a drift region in the substrate. In some embodiments, the substrate is a silicon-on-insulator (SOI) substrate. Operation 202 relates to the formation of a drift region 304, as described below in FIG. 3A.

In some embodiments, covering the substrate with a layer of patterning material comprises depositing a layer of photoresist on the top surface of the substrate. In some embodiments, covering the substrate with a layer of patterning material comprises depositing a layer of hardmask material over the top surface of the substrate, followed by depositing a layer of patterning material. Operation 202 includes steps associated with transferring a pattern to the layer of patterning material, and developing the patterning material to form openings therein which expose the top surface of the substrate. In some embodiments, transferring a pattern to the layer of patterning material comprises performing a photolithography process and develop process to create openings in the layer of mask material which correspond to the locations of drift regions in the substrate. In some embodiments, transferring a pattern to the layer of patterning material comprises performing an electron beam or ultraviolet pattern transfer process, and developing the patterning material to form openings therethrough. In embodiments of operation 202 which comprise steps directed to depositing a layer of hardmask material over the top surface of the substrate, the operation further comprises steps associated with performing an etch process to remove portions of the layer of hardmask material exposed by the openings in the layer of patterning material (such as, e.g., an isotropic plasma etch process) to expose the substrate below the layer of hardmask material.

In some embodiments, the doping process comprises depositing a layer of epitaxial material over the substrate in the opening of the layer of mask material, and annealing the substrate to promote migration of the dopants from the layer of epitaxial material in to the substrate to form the drift region.

In some embodiments, the doping process comprises performing an implant process with dopant atoms to create the drift region. In some embodiments, the dopant atoms are N-type atoms such as phosphorous (P) or arsenic (As). In some embodiments, the dopant atoms are P-type atoms such as boron (B) or gallium (Ga). Implanting dopant atoms into the substrate involves steps associated with regulating the implant angle ($\theta_{drift}$) and implant energy (keV) to regulate the shape and depth of the drift region, and the implant duration (seconds) in order to regulate the dopant concentration in the drift region. In some embodiments, the implant process include steps directed to forming a drift region the drift region has a depth of not less than 50 nanometers (nm), and not more than 200 nm. In some embodiments, the drift region includes a dopant concentration of not less than $1 \times 10^{10}/cm^2$ and not more than $1 \times 10^{11}/cm^2$. In some embodiments where the drift region has a thickness of less than 50 nm, the implant process to form the drift wells becomes complex in order to form multiple doped zones in the drift region. In embodiments where the drift region has a thickness greater than 200 nm, no additional benefit is derived in terms of reduced leakage current or process flexibility as compared to drift regions with thicknesses between 100 nm and 200 nm. In embodiments where the dopant concentration is less than $1 \times 10^{10}/cm^2$ the low dopant concentration makes it more difficult to switch the transistor to an ON state and the drift region contributes to the overall resistance of the integrated circuit. In embodiments where the drift region has a dopant concentration of more than $1 \times 10^{11}/cm^2$ no additional benefit is derived in terms of promoting rapid switching of the transistors. In LDMOS devices, the drift region has a dopant concentration smaller than the dopant concentration in any of the doped zones of the drain well.

In operation 202, after the doping process, the layer of patterning material (and any hardmask material deposited on the substrate) is removed and the substrate is prepared for other operations of the method.

Figure 3A:
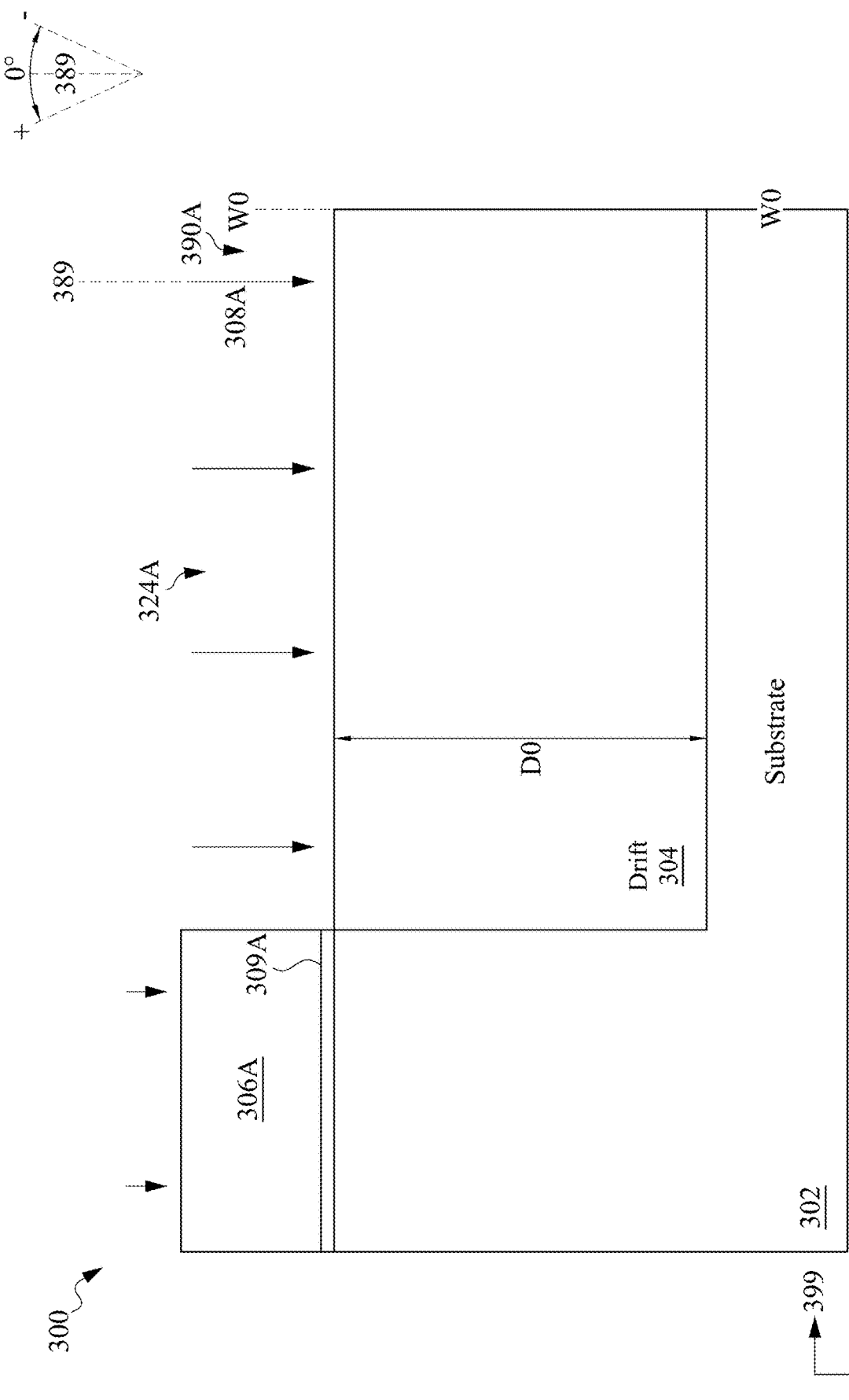
FIGS. 3A-3J are cross-sectional views of a LDMOS during a manufacturing process, in accordance with some embodiments.

FIG. 3A is a cross-sectional view of an integrated circuit 300 during a manufacturing process, in accordance with some embodiments. Elements of integrated circuit 300 which have a similar structure and/or function as the elements of integrated circuit 100, described above, have a same identifying numeral, incremented by 200.

In FIG. 3A, substrate 302 is a semiconductor substrate with a drift region 304 therein. Substrate 302 is a P-doped silicon substrate. In some embodiments, the substrate is silicon, silicon germanium, GaAs, or some other semiconductor material suitable for manufacturing LDMOS devices. Drift region 304 is doped with N-type dopants to have a surplus of N-type dopants with respect to the concentration of P-type dopants in the substrate 302. Drift region 304 has a drift region depth D0 measured from the top surface of substrate 302 to the bottom of drift region 304. In FIG. 3A, W0 indicates the edge of the drift region 304.

A layer of patterning material 306A is deposited over the substrate 302, with an opening 324A in the layer of patterning material 306A, exposing the top surface of substrate 302. A hardmask 309A is between patterning material 306A and the top surface of substrate 302. Opening 324A extends through both patterning material 306A and hardmask 309A.

Dopant atoms are implanted along an implant vector 308A with an implant angle 390A with respect to a reference line 389 normal to the top surface of the substrate 302 (and the top surface of drift region 304). Implant vector 308A is at 0° from reference line 389. In some embodiments, the implant vector for dopant atoms has an implant angle which is not greater than 10° and not less than −10° from reference line 389. In the implant process to form a drift region, a near-vertical (e.g., ~0°) implant angle provides the most precise dimensional control of the distance between the edge of the drift region and the source or drain well in the substrate near the drift region. Implant angles which deviate from vertical (e.g., with an implant angle of >|±10°|) incur a broadening of the drift region which introduces a shift in switching time of the transistors in the integrated circuit.

The implanting of dopant atoms occurs along an implant vector at an implant angle from a reference line normal to the top surface of the substrate in a plane which extends in the second direction 399 (see below, see also second direction 199 in FIG. 1, above). An implant vector with no offset (i.e., implant angle=0°) from the reference line indicates that atoms approach the surface normal to the surface. An implant vector with a negative implant angle with regard to the reference line indicates that atoms approach the surface with a component of motion from the drift region (or the space above the drift region) toward the position of the gate electrode. An implant vector with a positive implant angle with regard to the reference line indicates that atoms approach the surface with a component of motion from the drift region (or the space above the drift region) away from the gate electrode. In some embodiments, dopant atoms for the drift region are implanted with an implant vector having a zero-degree (0°) implant angle or a positive implant angle.

Patterning material 306A is a layer of photoresist. In some embodiments, patterning material is a layer of dielectric material (e.g., silicon dioxide, silicon nitride, and the like) which has been etched to form an opening over the substrate at the position of the drift region. In some embodiments, a layer of dielectric material is used as the patterning material because the implant process has a high implant energy to drive dopant atoms deep into the substrate and photoresist is inadequate to shield the substrate in the area of a source well (see source well 110 in FIG. 1) from the drift region dopant atoms.

Method 200 includes an operation 204, wherein a source well is formed in a substrate. Operation 204 includes steps directed toward covering the substrate with a layer of patterning material, steps directed toward transferring a pattern to the layer of patterning material, modifying the patterning material to form openings therein, and steps directed toward performing a doping process to create the source well in the substrate. Operation 204 is related to the formation of a source region 310, as described below in FIG. 3B.

In some embodiments, covering the substrate with a layer of patterning material comprises depositing a layer of photoresist on the top surface of the substrate. In some embodiments, covering the substrate with a layer of patterning material comprises depositing a layer of hardmask material over the top surface of the substrate, followed by depositing a layer of patterning material. In some embodiments, transferring a pattern to the layer of patterning material comprises, performing a photolithography process and develop process to create openings in the layer of mask material which correspond to the locations of drift regions in the substrate. In some embodiments, transferring a pattern to the layer of patterning material comprises performing an electron beam or ultraviolet pattern transfer process, and developing the patterning material to form openings therethrough. In embodiments of operation 204 which comprise steps directed to depositing a layer of hardmask material over the top surface of the substrate, the operation further comprises steps associated with performing an etch process to remove portions of the layer of hardmask material exposed by the openings in the layer of patterning material (such as, e.g., an isotropic plasma etch process) to expose the substrate below the layer of hardmask material.

In some embodiments, the doping process comprises depositing a layer of epitaxial material over the substrate in the opening of the layer of mask material, and annealing the substrate to promote migration of the dopants from the layer of epitaxial material in to the substrate to form the source well.

In some embodiments, the doping process comprises performing an implant process with dopant atoms to create the source well. In some embodiments, the dopant atoms are N-type atoms such as phosphorous (P) or arsenic (As). In some embodiments, the dopant atoms are P-type atoms such as boron (B) or gallium (Ga). In steps directed toward the doping process, the source well is doped by adding dopants of the opposite type to the dopants in the drift region.

Implanting dopant atoms into the substrate for the source well involves regulating the implant angle ($\theta_{source}$) and implant energy (keV) to regulate the shape and depth of the source well, and the implant duration (seconds) in order to regulate the dopant concentration in the source well. In some embodiments, the dopant atoms of the source well (see source well 310) are added to the substrate with a normal implant vector (e.g., approaching the substrate with no lateral motion, such that dopant atoms move directly down into the substrate, forming a vertical interface between the source well and the drain well. By avoiding overlap of the source well and the drift region, the resistance to switching an LDMOS device to an "on" state is reduced.

Figure 3B:
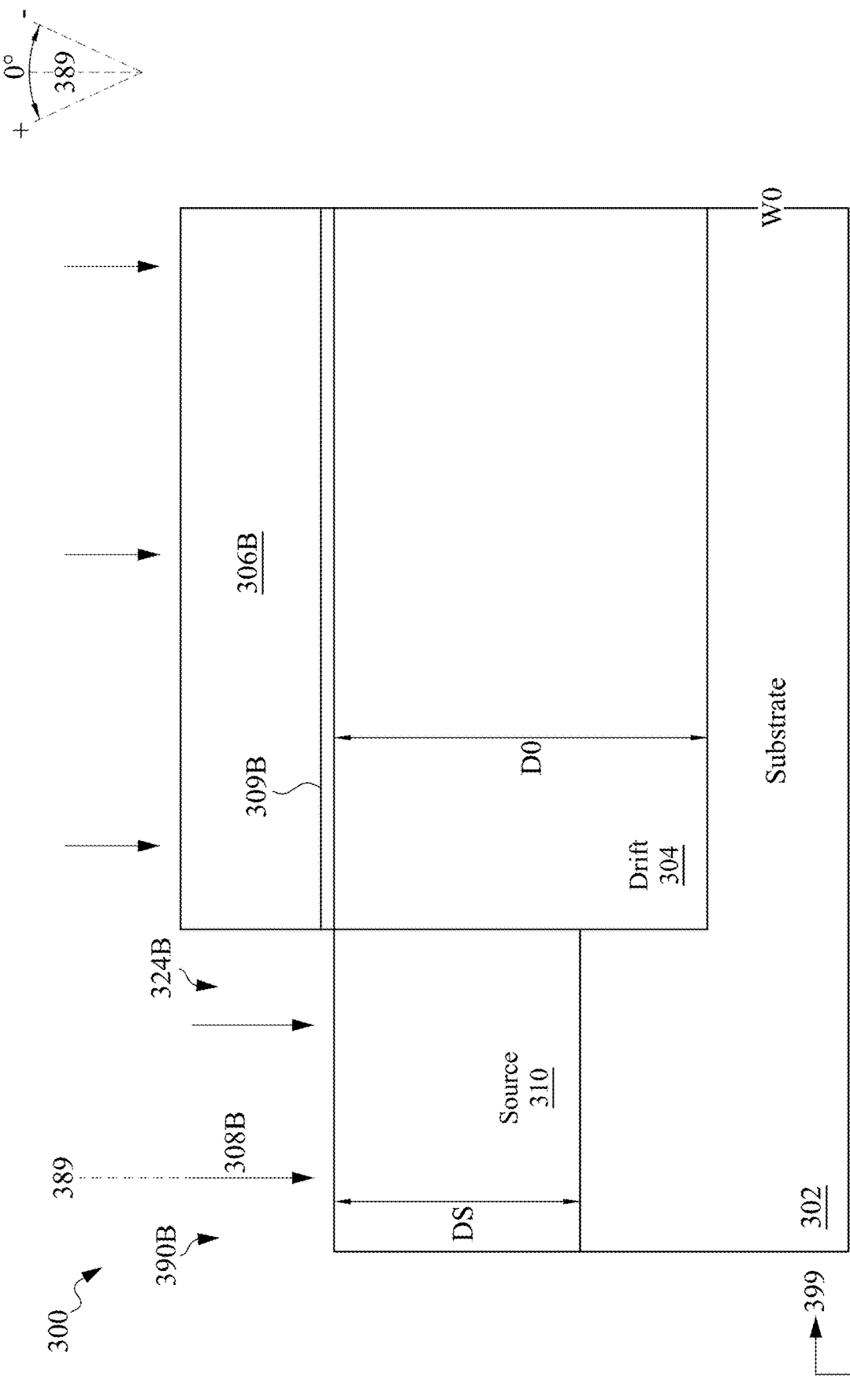

FIG. 3B is a cross-sectional view of an integrated circuit 300 during a manufacturing process, in accordance with some embodiments. Elements of FIG. 3B which have a same structure and/or function as elements of FIG. 3A have a same identifying numeral.

In FIG. 3B, a hardmask 309B is deposited over the top surface of substrate 302, and a layer of patterning material 306B is deposited over hardmask 309B. An opening 342B extends through the layer of patterning material 306B and through the hardmask 309B, exposing a top surface of substrate 302. Dopant atoms are deposited with an implant vector 308B substantially parallel to reference line 389 (e.g., implant angle 390B is 0°) such that source well 310 extends down in to substrate a source well depth DS. Source well depth DS is smaller than drift region depth D0. In some embodiments, DS>D0. Source well 310 adjoins drift region 304 with a border which extends in the first direction 398.

Patterning material 306B is a layer of photoresist. In some embodiments, patterning material 306B is a patterning material compatible with electron beam lithography, ultraviolet (UV) lithography, or some other pattern transfer technique known to practitioners of semiconductor manufacturing arts.

Method 200 includes an operation 206, wherein a gate electrode is formed over a top surface of the substrate. Operation 206 includes steps directed toward depositing gate dielectric material over the top surface of the substrate. Operation 206 also includes steps directed toward depositing a gate electrode material over the gate dielectric material. Operation 206 includes steps directed toward performing a patterning process and an etch process to form at least one gate electrode over the top surface of the substrate. Operation 206 is related to the formation of a gate electrode, as described in FIG. 3C, below, where the gate electrode includes a gate dielectric 311, a gate electrode material 312, and a spacers 314.

Steps directed toward depositing gate dielectric material over the top surface of the substrate include, e.g., steps related to chemical vapor deposition (CVD) or atomic layer deposition (ALD) of a dielectric material over the top surface of the substrate. In some embodiments, the deposited dielectric material is silicon dioxide. In some embodiments, the deposited dielectric material is an aluminum oxide material. In some embodiments, the deposited dielectric material is a high-κ (κ=dielectric constant) material, with κ of at least 3.2.

Steps directed toward depositing a gate electrode material over the gate dielectric material include steps related to depositing a semiconductor material over the top surface of the substrate. In some embodiments, the gate electrode material is a type IV semiconductor material. In some embodiments, the gate electrode comprises polysilicon or some other semiconductor material suitable for an LDMOS device in an integrated circuit. In some embodiments, the gate electrode material is a dummy gate electrode material, which is used to regulate the position of spacers (see below) for forming the doped zones in the drain well of an LDMOS device.

Performing a patterning process includes steps directed toward depositing a layer of patterning material over the gate electrode material, transferring a pattern to the layer of patterning material, and modifying the layer of patterning material by forming openings according to the transferred pattern, wherein the remaining portions of the patterning material correspond to portions of the surface of the substrate to be retained as a gate electrode for, e.g., an LDMOS device of the semiconductor device.

Steps directed toward performing an etch process include performing an etch process to remove exposed portions of the gate electrode, (and subsequently exposed portions of gate dielectric material) to expose the substrate, including at least some of the source well and the drift region of each LDMOS device of the semiconductor device. Operation 206 also includes steps directed to preparing the surface for other operations of the method 200.

Operation 206 further includes steps directed toward forming a spacer on the sides of the gate electrode material and the gate dielectric material to electrically isolate gate electrode material from other electrical components in the LDMOS device. In some embodiments, steps directed toward forming a spacer include performing a conformal deposition of dielectric material (spacer material) over the gate electrode material and the substrate, and performing an anisotropic etch process to expose the substrate and the top surface of the gate electrode material, leaving a portion of spacer material on the sides of the gate electrode material and the gate dielectric material. A cross-sectional diagram of a gate electrode and gate dielectric material consistent with the performance of operation 206 is provided in FIG. 3C, below.

Figure 3C:
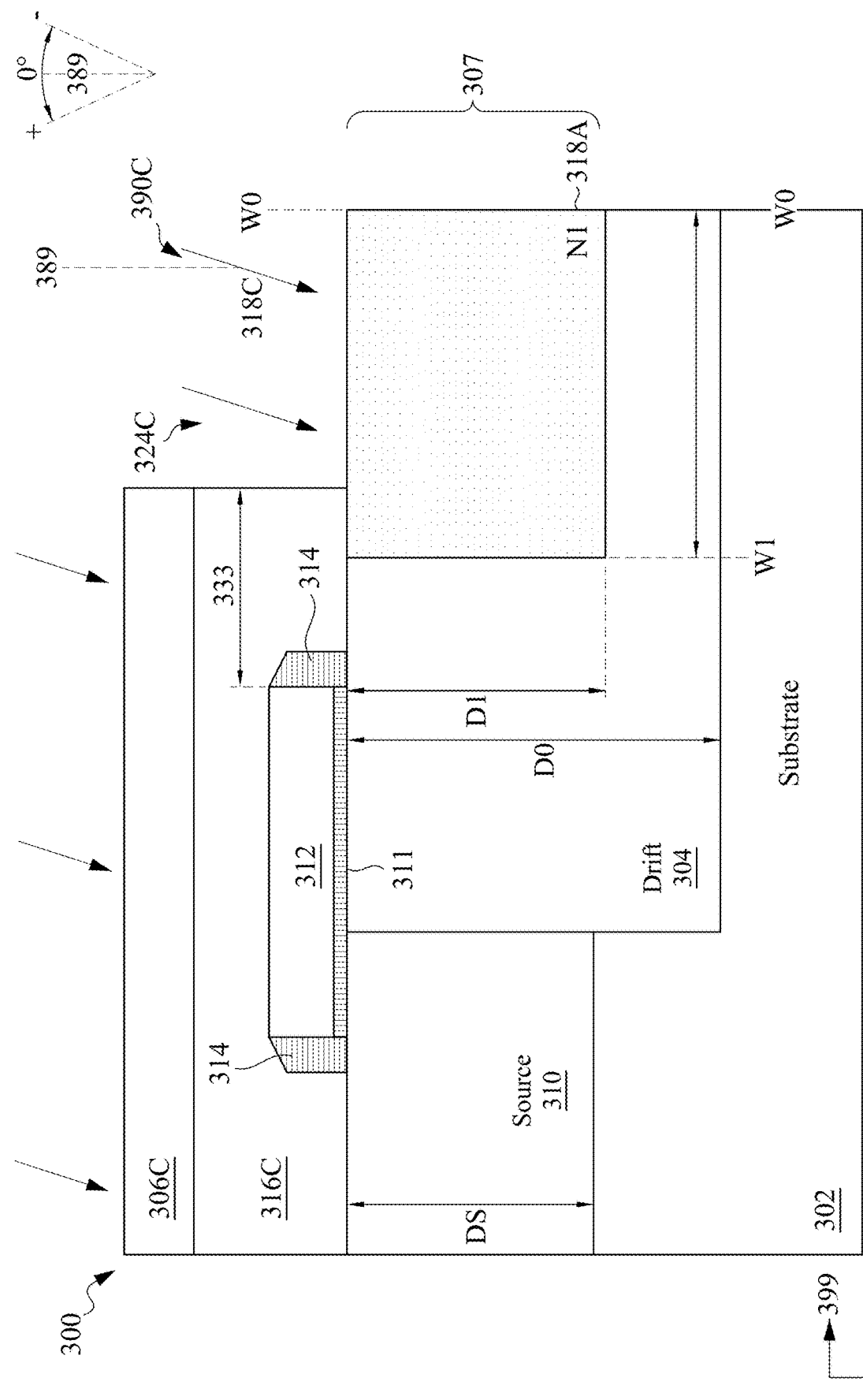

FIG. 3C is a cross-sectional view of an integrated circuit 300 during a manufacturing process, in accordance with some embodiments. In FIG. 3C, gate dielectric 311 is directly against substrate 302 over the source well 310 and the drift region 304, and the interface between source well 310 and drift region 304. In some embodiments, gate dielectric 311 is a layer of silicon dioxide. In some embodiments, gate dielectric 311 is a high-κ dielectric material, or some other dielectric material suitable to electrically isolate a gate electrode material 312 from the source well 310 and the drift region 304d.

Method 200 includes an operation 208, wherein doped zones of a drain well are formed. Cross-sectional diagrams of a semiconductor device during a manufacturing process which includes steps of forming doped zones are provided in FIGS. 3C-3F, as described below.

Operation 208 includes steps directed toward depositing a layer of mask material over the substrate and the gate electrode, steps directed toward depositing layer of patterning material over the mask layer, and steps related to forming an opening in the layer of patterning material and layer of mask material. Operation 208 also includes steps directed toward performing a doping process to form the drain well, or a doped zone of the drain well. FIG. 3C provides a non-limiting exemplary embodiment of mask material 316C over a top surface of the substrate 302, consistent with performance of operation 208.

According to a design specification for an LDMOS device, two or more doping processes are performed to form the drain well of an integrated circuit. In some embodiments, the two or more doping processes have different implant vectors or implant angles. In some embodiments, the two or more doping processes have different implant depths (e.g., the doped zones have different zone depths). A pattern of adjusting the implant angle and implant depth, and the addition of a spacer on a mask layer to shift the opening through which dopant atoms are added, produces multiple doped zones which act as the drain of a semiconductor device.

Steps related to depositing a layer of mask material over the substrate include depositing a dielectric material over the top surface of the substrate. In some embodiments, the dielectric material is silicon dioxide. In some embodiments, the dielectric material is one of silicon nitride, silicon oxy-nitride, spin on glass, boron phosphorus silicon glass (BPSG), fluorinated silica glass (FSG), or a hardmask material suitable for front-end integration schemes for a semiconductor device. The mask material is sufficiently dense to resist impact from dopant atoms which are directed to the substrate to form the doped zones of the drain well. The mask material is used in one or more doping processes in making the LDMOS device. Thus, a mask material with higher density is better able to protect the drift region of the LDMOS device without eroding or fracturing.

Steps related to depositing a layer of patterning material over the mask layer include steps associated with depositing photoresist or a patterning material compatible with electron beam, ultraviolet (UV) patterning, and other patterning techniques familiar to semiconductor manufacturing.

Steps related to forming an opening in the layer of patterning material and the layer of mask material include performing a photolithography process and a develop process, performing an electron-beam lithography process and a develop process, or performing an ultraviolet (UV) lithography process, or some other pattern transfer process compatible with LDMOS device manufacture.

Steps related to a doping process to form the drain well include either a process of depositing an epitaxial layer of dopant-atom containing material over the substrate in the opening formed in the mask layer/patterning material and performing an anneal process to drive dopants into the substrate (as described above), or a process of implanting dopant atoms from a dopant atom source.

In some embodiments, the doping process comprises performing an implant process with dopant atoms to create the drift region. In some embodiments, the dopant atoms are N-type atoms such as phosphorous (P) or arsenic (As). In some embodiments, the dopant atoms are P-type atoms such as boron (B) or gallium (Ga). Implanting dopant atoms into the substrate involves steps associated with regulating the implant angle ($\theta_{drain\_zone}$) and implant energy (keV) to regulate the shape and depth of the drift region, and the implant duration (seconds) in order to regulate the dopant concentration in the drift region. In some embodiments, the implant angle ranges from 0° to +60°. In some embodiments, the implant angle ranges from 0° to −60°. Implant angles more extreme than ±60° have a greater likelihood of overlapping another doped zone in the drain well during the manufacturing process. The implant angle is related to the angle of the edge of the sidewall closest to the source in the integrated circuit. An implant angle for an implant process is selected according to pattern of the edge angles of the doped zones in the drain well. For example, see FIG. 5C, the doped zones 518A-518D in drain well 507 of integrated circuit 500 have both vertical and non-vertical edges of the doped zones, alternating: vertical, non-vertical, vertical, non-vertical. In FIG. 5D, the doped zones 518A-518D in drain well 507 of integrated circuit 501 have both vertical and non-vertical edges closest to source 507, alternating non-vertical, vertical, non-vertical, vertical. In FIG. 5E, all of the doped zones 518A-518D of integrated circuit 502 have non-vertical edges closest to the source 507, alternating as: negative angle, positive angle, negative angle, positive angle. The implant angle of dopant atoms added to a substrate alternates between implants, or the spacing between the implant boundaries of subsequent implants alternates, in order to provide spatial resolution between the doped zones of the drain well. For example, in some embodiments, a first doped zone is formed with a negative implant angle (−) and a second doped zone is formed with a normal (0°) implant angle. In some embodiments, a first doped zone is formed with a normal implant angle (0°) and a second doped zone is formed with a positive (+) implant angle In some embodiments, a first doped zone is formed with a positive implant angle (+) and a second doped zone is formed with a negative (−) implant angle. In some embodiments, a first doped zone is formed using a first implant shield (e.g., mask layer 316C) at a positive (+) implant angle, a normal (0°) implant angle, or a negative (−) implant angle, and a second doped zone is formed using a second implant shield (e.g., spacer 320) with a positive (+) implant angle, a normal (0°) implant angle, or a negative (−) implant angle. A pattern of alternating implant angles and implant shields is adjusted according to a specification of an LDMOS device being manufactured. For example, in some embodiments, the implant angle of a second implant and a fourth implant are adjusted to be positive (+) such that there is a separation between the top edges of zones on either side of the second doped zone and/or the third doped zone (see, e.g., FIG. 5E, below).

A number of implant processes performed to form the LDMOS device is determined according to a semiconductor device specification used by a manufacturer during a manufacturing process. In some embodiments of the method, the doping process is performed two times, three times, four times, or more times, in order to form the doped well. In some embodiments, the doping process for a doped zone of the drain well is performed with a 0° implant angle. In some embodiments, the doping process for a doped zone of the drain well is performed with a negative implant angle. In some embodiments, the doping process for a doped zone of the drain well is performed with a positive implant angle. In some embodiments, as described further below, the drain well is formed with alternating implant angles to form the doped zones thereof. FIGS. 3C-3F are described hereafter to clarify the order of performing steps to form an LDMOS device having four doped zones. FIGS. 4A-4B and FIGS. 5A-5E describe alternative embodiments of LDMOS devices with positive, negative, and 0° (normal) implant angles manufactured according to the method described below.

Each doped zone of a drain well has an associated implant vector, zone depth (related to implant energy), and implant dose to achieve a dopant concentration and zone profile for the doped zone of the drain well. For example, a doped zone having a normal implant angle (e.g., a 0° implant angle) has a boundary closest to the source well which extends straight down from the top surface of substrate (see, e.g., doped zone 318B (zone N2) of drain well 307 in FIG. 3B). A doped zone having a positive implant angle has a boundary closest to the source well which is closer to the source well at the top surface of the substrate, and farther from the source well at deeper into the substrate (see doped zone 518D (zone N4) of drain well 507 in FIG. 5D). A doped zone having a negative implant angle has a boundary closest to the source well which is closer to the source well deep in the substrate, and farthest from the source well at the top surface of the substrate (see, e.g., doped zone 518A (zone N1) of drain well 507 in FIG. 5A).

A first doped zone receives a first zone implant dose to a first zone dopant concentration from dopant atoms added at a first implant vector with a first implant angle. The first zone dopant concentration results from the drift region implant dose plus the first zone implant dose. A second doped zone receives a second zone implant dose to a second zone dopant concentration from dopant atoms added at a second implant vector with a second implant angle. The second zone dopant concentration is the result of the first implant dose and the second implant dose. Each subsequent implant dose achieves an implant concentration in which is the sum of the previous implant doses into the volume being dosed by the implant processes, including the drift region implant dose (e.g., the third doped zone has a third dopant concentration which is the result of the third dose plus the second dose plus the first dose plus the drift zone dose).

Figure 3D:
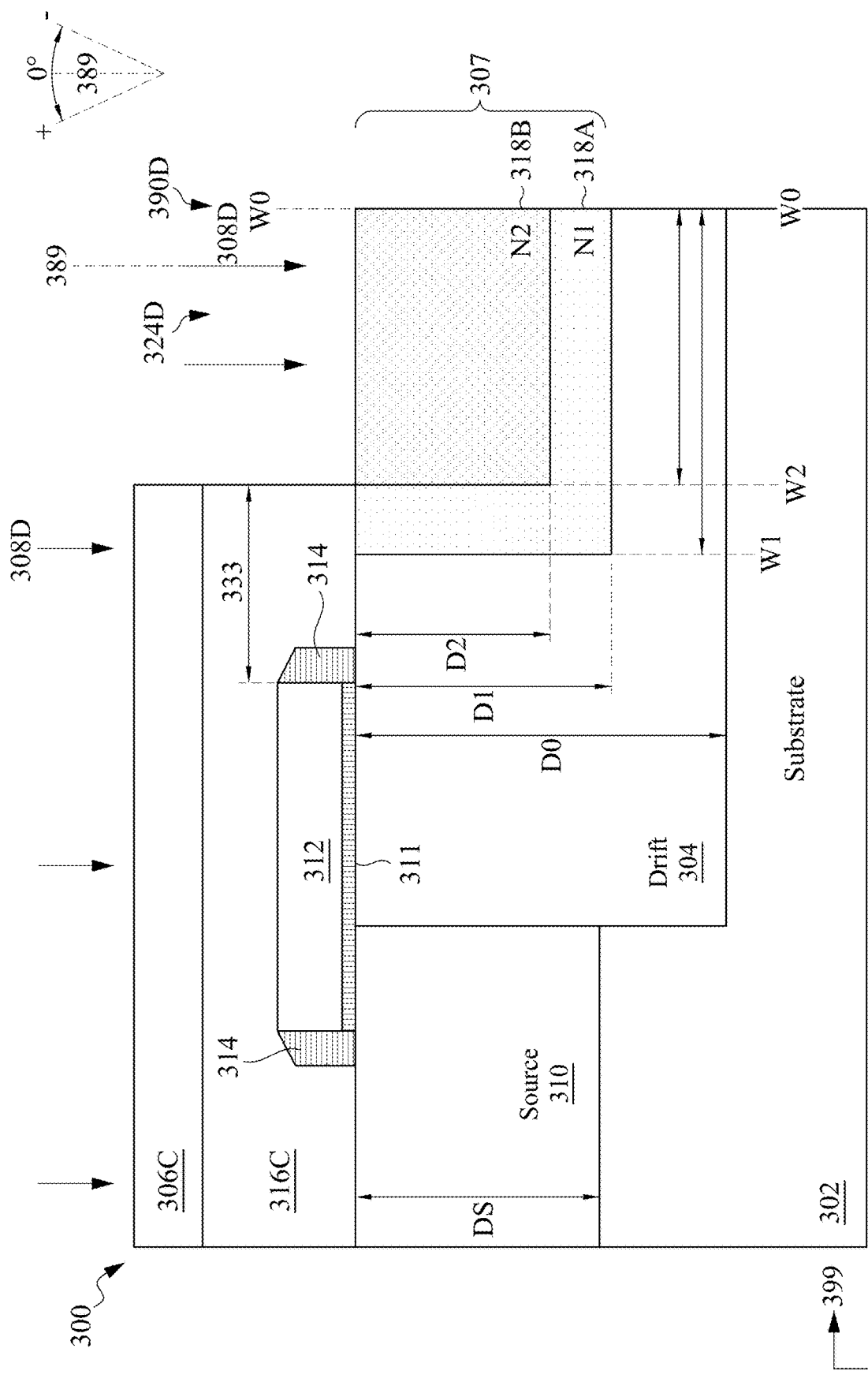
Figure 3E:
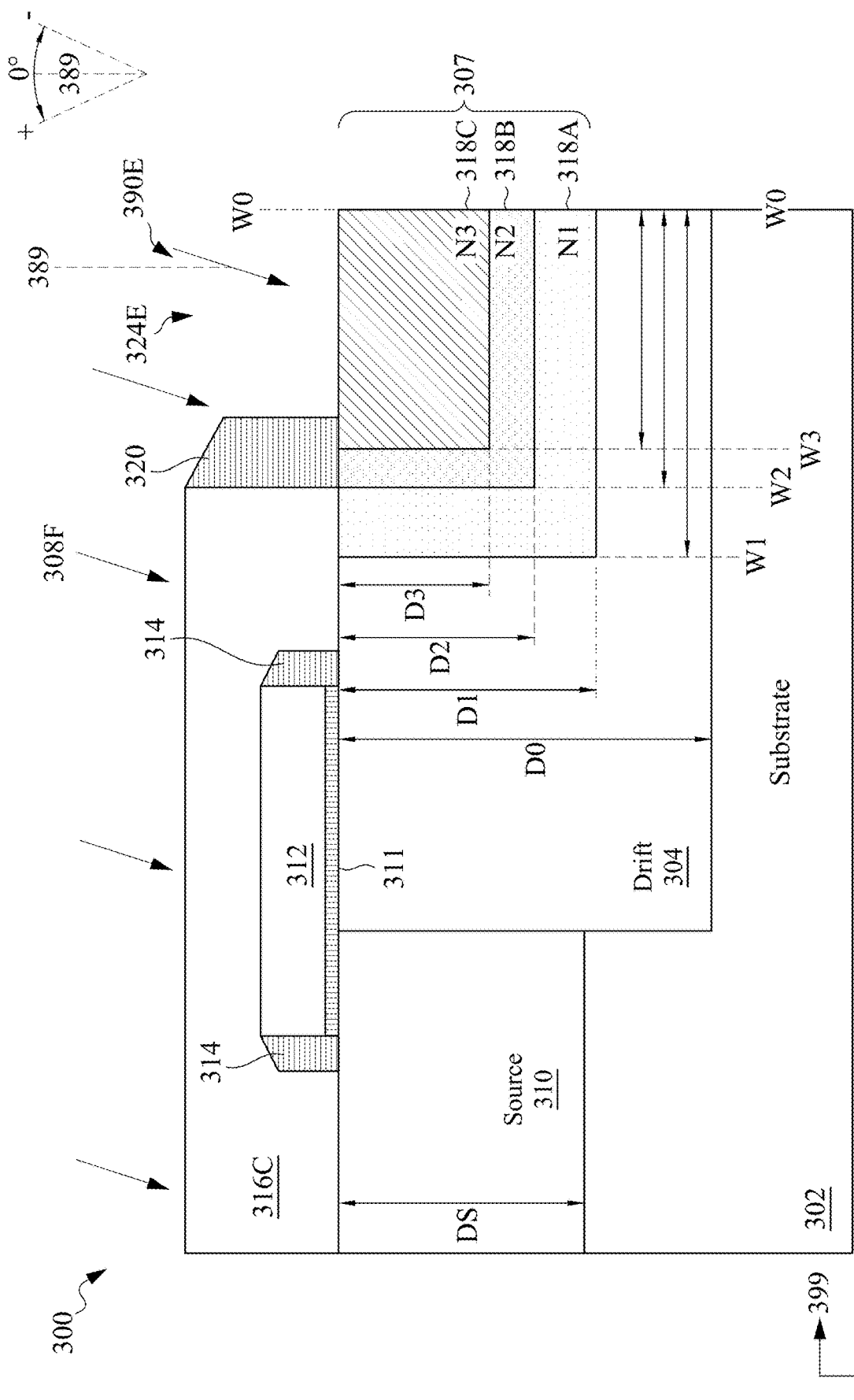
Figure 3F:
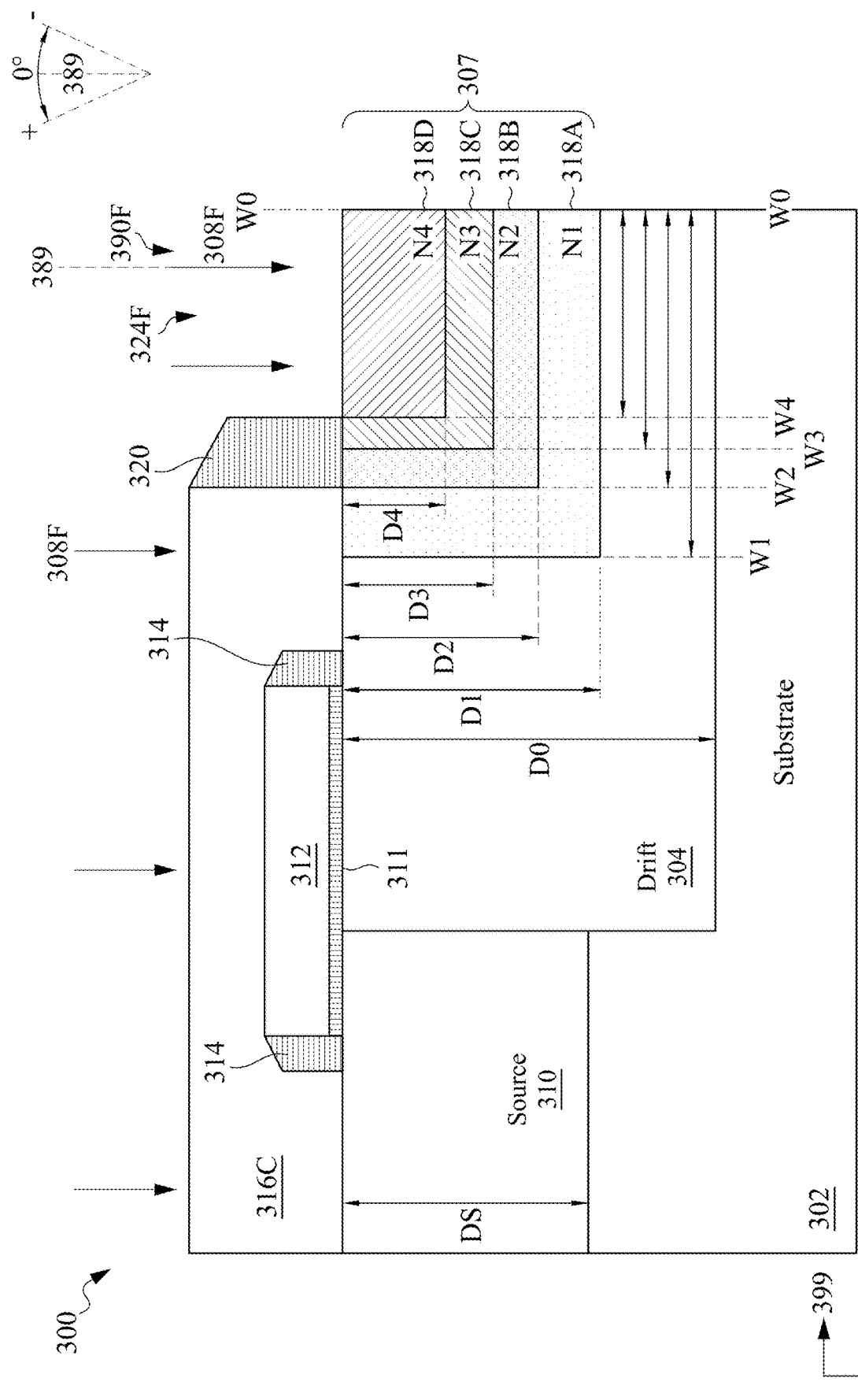

In some embodiments, the doped zones of a drain well are implanted to different depths (see, e.g., FIG. 3F depths D1-D4, where D1>D2>D3>D4). In some embodiments, the doped zones of a drain well are implanted to a same depth, but have different associated implant angles (see, e.g., FIG.

5C, where doped zones alternate between negative and normal (e.g., 0°) implant angles, FIG. 5D, where doped zones alternate between normal and positive implant angles, or FIG. 5E, where doped zones alternate between negative and positive implant angles).

In some embodiments, two doped zones are implanted with a single mask layer over the substrate. In some embodiments, a spacer is added to the sidewall of the mask layer to advance the sidewall of the mask layer away from the source well and toward the drain well (or, toward the drain LDD zone position), protecting the first implant zone and/or the second implant zone from subsequent dopant atom implantation (see, e.g., spacer 320 against mask layer 316 in FIG. 3E, as described below).

FIGS. 3C-3F are cross sectional views of an integrated circuit 300 during a manufacturing process, in accordance with some embodiments.

In FIG. 3C, a layer of mask material 316C has been deposited over gate electrode material 312 and spacers 314 on the source well side and the drain well side of the gate electrode. A layer of patterning material 306C is over the top surface of the layer of mask material 316C. An opening 324C extends through layer of mask material 316C and the layer of patterning material 306C to expose the top surface of substrate 302 in the drift region 304. Dopant atoms are added in an implant process along implant vector 308C at an implant angle 390C from reference line 389. First doped zone 318A extends down a first zone depth D1 from the top surface of drift region 304, as a first part of doped drain 307.

In some embodiments, the first doped zone 318A is doped with dopant atoms on an implant vector of 0° to 60°. In some embodiments, the implant energy of the doped atoms is relatively high (50-1000 keV), and the dopant atoms are added to a low concentration of not less than about $1\times10^{12}/cm^2$ to not more than about $1\times10^{16}/cm^2$ of dopant atoms. Implant energies larger than 1000 keV are more likely to damage the substrate and induce excess diffusion during anneal processes to heal damage to the substrate. Implant energies smaller than 50 keV are likely to leave small manufacturing margins for implant processes making the second, third, and/or fourth doped zones of a drain well. The range of dopant concentrations for implants into a first doped zone is sufficient to create a concentration gradient at a border between, e.g., the doped zone and the drain well, or the doped zone and a doped zone with a higher dopant concentration (e.g., a second, third, or fourth implant zone).

In FIG. 3D, opening 324D extends through layer of patterning material 306C and layer of mask material 316C. Dopant atoms are added along implant vector 308D at implant angle 390D from reference line 389. Implant angle 390D is a normal (0°) implant angle. Doped zone 318B has been formed in substrate 302, within doped zone 318A, extending downward a zone depth D2 from the top surface of the substrate 302, and having a zone width W2 from the edge of the drain well D0. Zone depth D2 is smaller than zone depth D1. In some embodiments, zone depth D2 is the same depth as zone depth D1.

In FIG. 3E, a spacer 320 has been added to the sidewall of layer of mask material 316C, forming a new opening 324E. Dopant atoms for doped zone 318C are added along implant vector 308E at an implant angle 390E from reference line 389. Doped zone 318C has a zone depth D3 extending downward from the top surface of the substrate 302, and a zone width W3 measured from the edge of the drain well D0. Doped zone 318C is separated from doped zone 318A by doped zone 318B. Doped zone 318C has a larger dopant concentration than doped zone 318B, doped zone 318A, and drift region 304. Spacer 320 shifts the edge of the implantable region of the drain well 307 away from the gate electrode, such that implants subsequent to formation of spacer 320 are also shifted away from the gate electrode, and the prior implants (e.g., into doped zones 318A and 318B) are protected, to have a set of sequentially increasing dopant concentrations in the doped zones between the drift region 304 and the drain LDD region (see drain LDD region 326A, in FIG. 3G). In some embodiments, spacer 320 has a thickness along the second direction 399 ranging from 2 nm to 20 nm, although other spacer thicknesses are also within the scope of the present disclosure. In some embodiments, the spacer 320 is manufactured by removing the patterning material 306C from the top surface of layer of mask material 316C, depositing a second dielectric material over the top surface of layer of mask material 316C, and performing a set of steps related to depositing patterning material, transferring a pattern to the patterning material, forming openings in the patterning material, and etching the second dielectric material to make large thickness spacers (e.g., greater than 100 nm in thickness).

In FIG. 3F, with spacer 320 on the side of layer of mask material 316C, dopant atoms are added along dopant vector 308F through opening 324F into substrate 302 to form doped zone 318D. Doped zone 318D is separated from doped zone 318B by doped zone 314C. Doped zone 318D has a dopant concentration which is grater than the dopant concentration of any of the drift region 304 or the doped zones 318A-318C. Doped zone 318D has a zone depth D4 extending downward from the top surface of substrate 302, and a zone width W4 from the edge of the drain well 307 (W0). In some embodiments, zone depth D4 is the same as zone depth D3. In some embodiments, zone depth D4 is smaller than zone depth D3. In FIG. 3F, the drain well 307 is complete, save for the drain LDD region (see drain LDD region 326A, in FIG. 3G). A drain LDD region is formed in the drain well according to operation 210 of method 200, Method 200 includes an operation 210, wherein LDD regions are formed in the substrate. Operation 210 relates to integrated circuit 300 of FIG. 3G and includes steps related to removing layer of mask material 316C and spacer 320 to expose substrate 302, spacer 314, and gate electrode material 312. Operation 210 also includes steps related to forming a hardmask material 309G on a top surface of substrate 302, depositing a layer of patterning material 306G over the hardmask material 309G, and transferring a pattern to the layer of patterning material 306G in order to form openings therein, exposing portions of the substrate (and the gate electrode) to for a doping process which forms the LDD regions in the source well and the drain well, and also adds dopant atoms to an exposed portion of the gate electrode material. Operation 210 also includes steps related to removing a layer of mask material and patterning material used to form a first set of LDD zones (regions) and depositing a second layer of patterning material, transferring a pattern thereto, forming openings in the second layer of patterning material, and performing a doping process into the source well to complete the formation of the source LDD region, as described below. In the discussion below, reference is made to the elements of FIGS. 3G and 3H for clarity in describing the positions of openings and films during the manufacturing process.

Steps related to removing the layer of mask material 306C and the spacer 320 to expose the substrate 302, the spacer 314, and the gate electrode material 312, are performed by, e.g., a liquid etch or wet etch process which removes the dielectric materials of the layer of mask material 306C and the spacer 320 without eroding the spacer 314 or the doped substrate. In some embodiments, an anneal process is performed on the substrate after each doped zone has been formed in the substrate, or in the drain well 307, to heal damage to the substrate caused by the doping process (the implanting of dopant atoms). In some embodiments, a single anneal process is performed after forming the drain well 307, and before performing the first LDD region implant process, in order to realign the atoms of the substrate and prevent erosion of the substrate due to the implant damage.

Steps related to forming a hardmask material (see hardmask material 309G) are related to forming a layer of silicon carbide, silicon nitride, or some other dielectric material which can be grown by, e.g., epitaxial deposition, on exposed semiconductor material, or deposited by chemical vapor deposition (CVD) onto the substrate and gate electrode, in order to protect portions of the source well and the doped zones (especially the low-dopant-concentration dopes zones) from the high dose implant process. A layer of patterning material is deposited over the hardmask material, and is patterned according to procedures employed in semiconductor device manufacturing (photolithography, UV lithography, electron beam lithography, and the like), and openings are formed therein according to the transferred pattern.

Forming openings in the layer of patterning material, and through the hardmask material, includes forming openings which correspond to positions of the LDD regions in the source well 310 and the drain well 307, and a portion of the gate electrode extending over the source well 310 and the drift region 304. Forming the openings also includes steps such as an etch process to remove the exposed hardmask material at the bottom of openings in the layer of patterning material and exposing the substrate in the source well 310 and the drain well 307, and the top surface of the gate electrode as described above (see first opening 324G1, and second opening 324G2 in FIG. 3G).

The doping process includes adding dopant atoms to form a drain well LDD region (see drain LDD region 326A), and a source well LDD zone (see source LDD zone 326C). Dopants are added through the first opening and the second opening along an implant vector 308G at an implant angle (see implant angle 390G). Dopant atom energy is regulated to keep the implant depth shallow and the implant dose high when making LDD regions of the LDMOS device.

Steps related to making source LDD zone 326D (e.g., finishing source LDD region 326B) include steps for removing the layer of patterning material (see patterning material 306G), the layer of mask material (see layer of mask material 316G), and steps for depositing a new layer of patterning material (see layer of patterning material 306H) and forming openings therein to expose the source well adjacent to the first source well LDD zone formed in the substrate.

A doping process to form the first source well LDD zone includes adding dopant atoms to the substrate at an implant angle which is normal (0°) or near-normal, to provide an interface between the first source well LDD zone and the second source well LDD zone (see source well LDD zones 326C and 326D of FIG. 3H) which is perpendicular to the top surface of the source well.

Figure 3G:
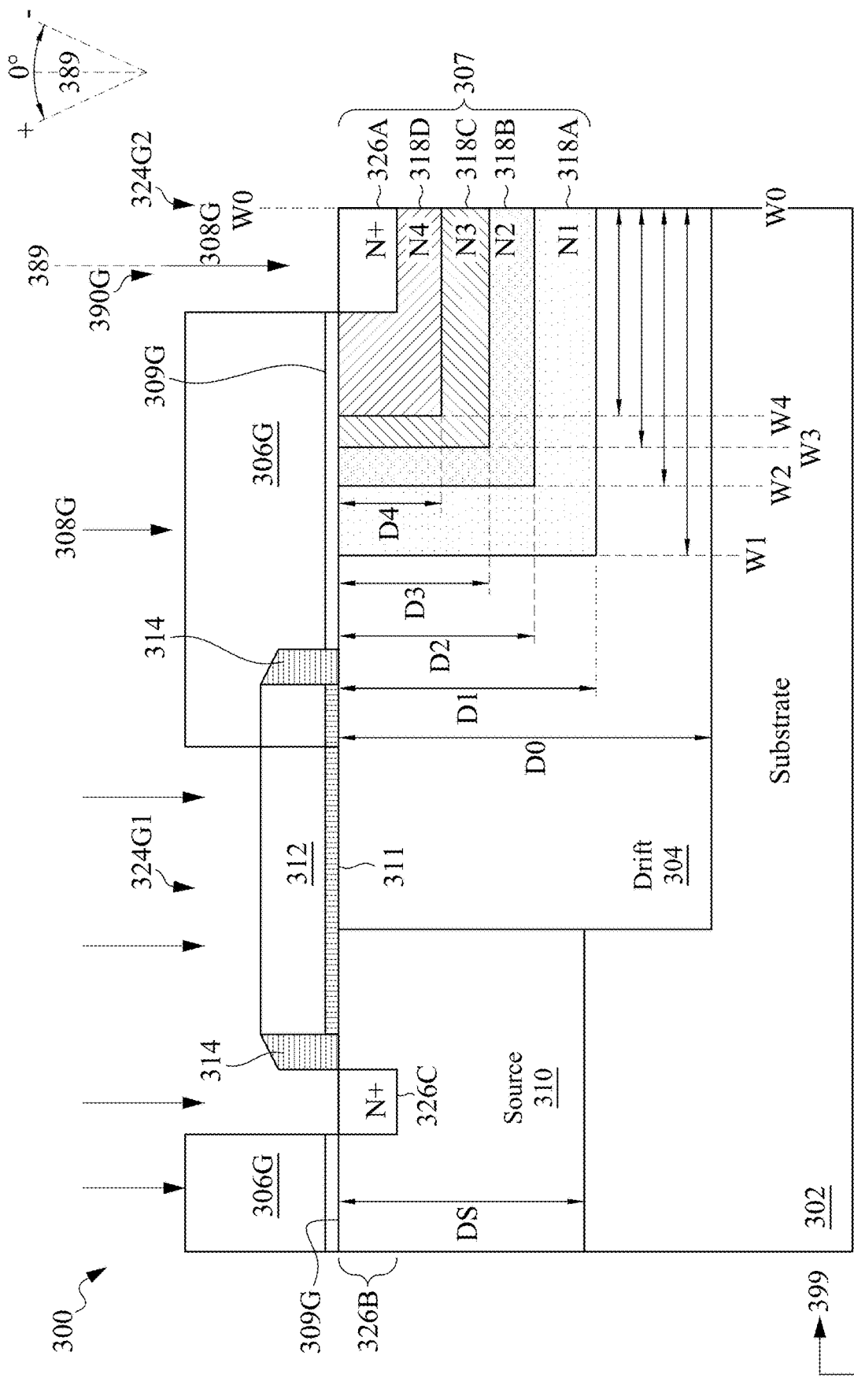
Figure 3H:
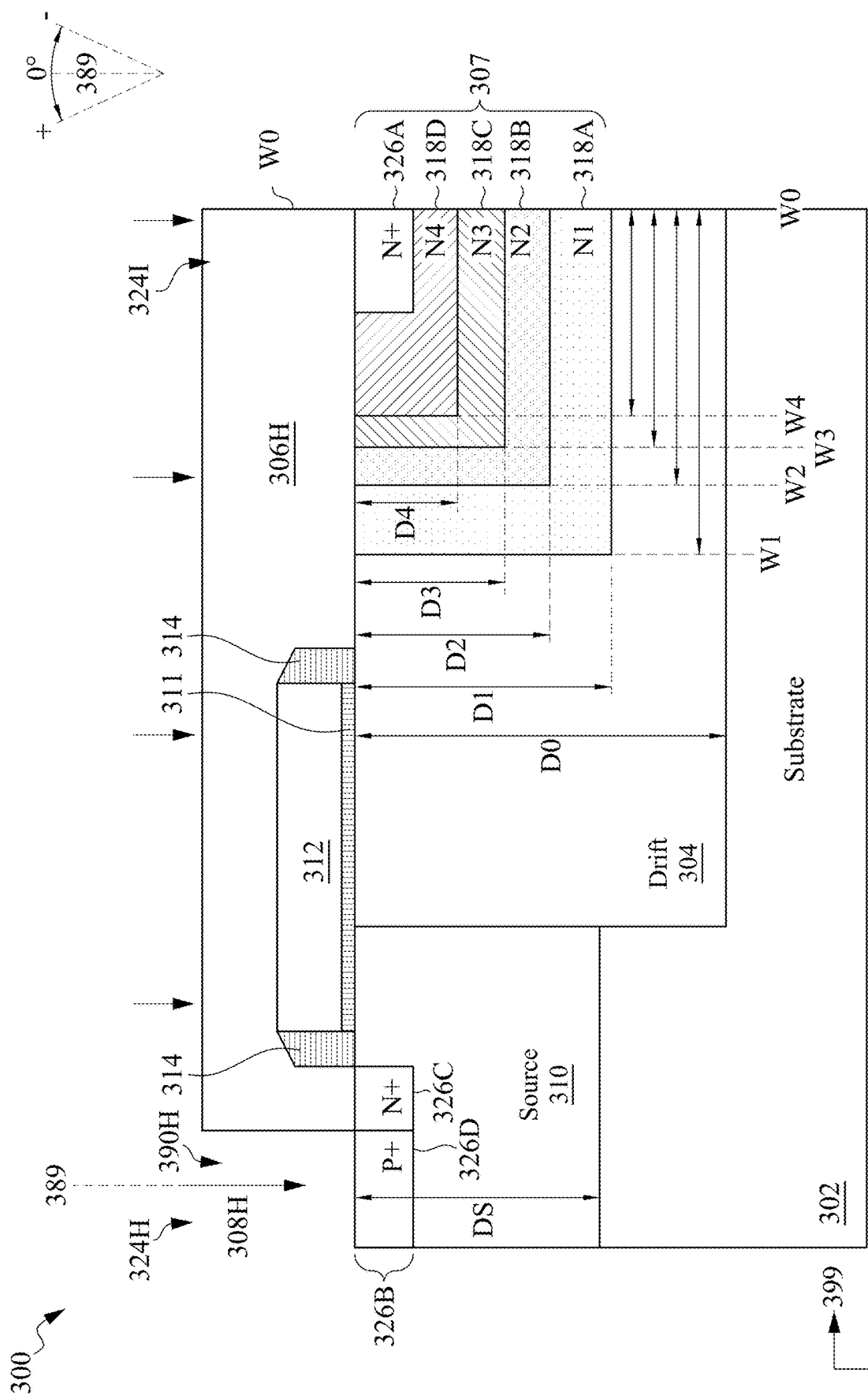

FIGS. 3G-3H are cross-sectional views of an integrated circuit 300 during a manufacturing process, in accordance with some embodiments.

In FIG. 3G, hardmask material 309G extends over the top surface of substrate 302 in the source well 310, the drift region 304, and the drain well 307. Layer of patterning material 306G is over the hardmask material 309G. First opening 324G1 extends through layer of patterning material 306G and hardmask material 309G to expose a portion of source well 310, spacer 314 on the source-well side of gate electrode material 312, and the gate electrode material 312 over the source well 310, and over the drift region 304. A portion of the gate electrode material 312 closest to the drain well 307, and the spacer 314 on the drain well side of gate electrode material 312, are covered by layer of patterning material 306C. Second opening 324G2 extends through layer of patterning material 306G and hardmask material 309G to expose a portion of drain well 307: doped zone 318D.

The first doping process to form LDD regions in an LDMOS device adds N-type dopant atoms to the substrate. Dopant atoms are added through second opening 324G2 along implant vector 308G, at an implant angle 390G from reference line 389 to form drain LDD region 326A in drain well 307. Dopant atoms are added to source well 310 through first opening 324G1 along implant vector 308G from reference line 389 to form source LDD zone 326C of source LDD region 326B. Implant angle 390D is a normal (0°) angle with regard to the reference line 389. Implanting dopant atoms into doped zone 318D is performed at an implant energy to add dopant atoms only to the doped zone 318D, and not to doped zones with lower concentrations of dopant atoms (e.g., doped zones 318C, 318B, or 318A).

In FIG. 3H, hardmask material 309G and layer of patterning material have been removed, and a layer of patterning material 309H has been deposited over drain well 307, gate electrode material 312, and source well 310. An opening 324H extends through layer of patterning material 306H to expose a portion of source well 310 adjacent to source LDD zone 326C. P-type dopant atoms are added to source well 310 to complete the source LDD region 326B. Dopant atoms are added along implant vector 308H at an implant angle 390H from reference line 389. Implant angle 390H is a normal angle (0° implant angle). Source LDD region 326B includes source LDD zone 326C, which includes a net surplus of N-type dopants, and which is adjacent to source LDD zone 326D, which includes a net surplus of P-type dopants. Layer of patterning material 306H protects gate electrode material 312 and drain well 307 from being implanted by P-type dopant atoms during formation of source LDD zone 326D.

Figure 3I:
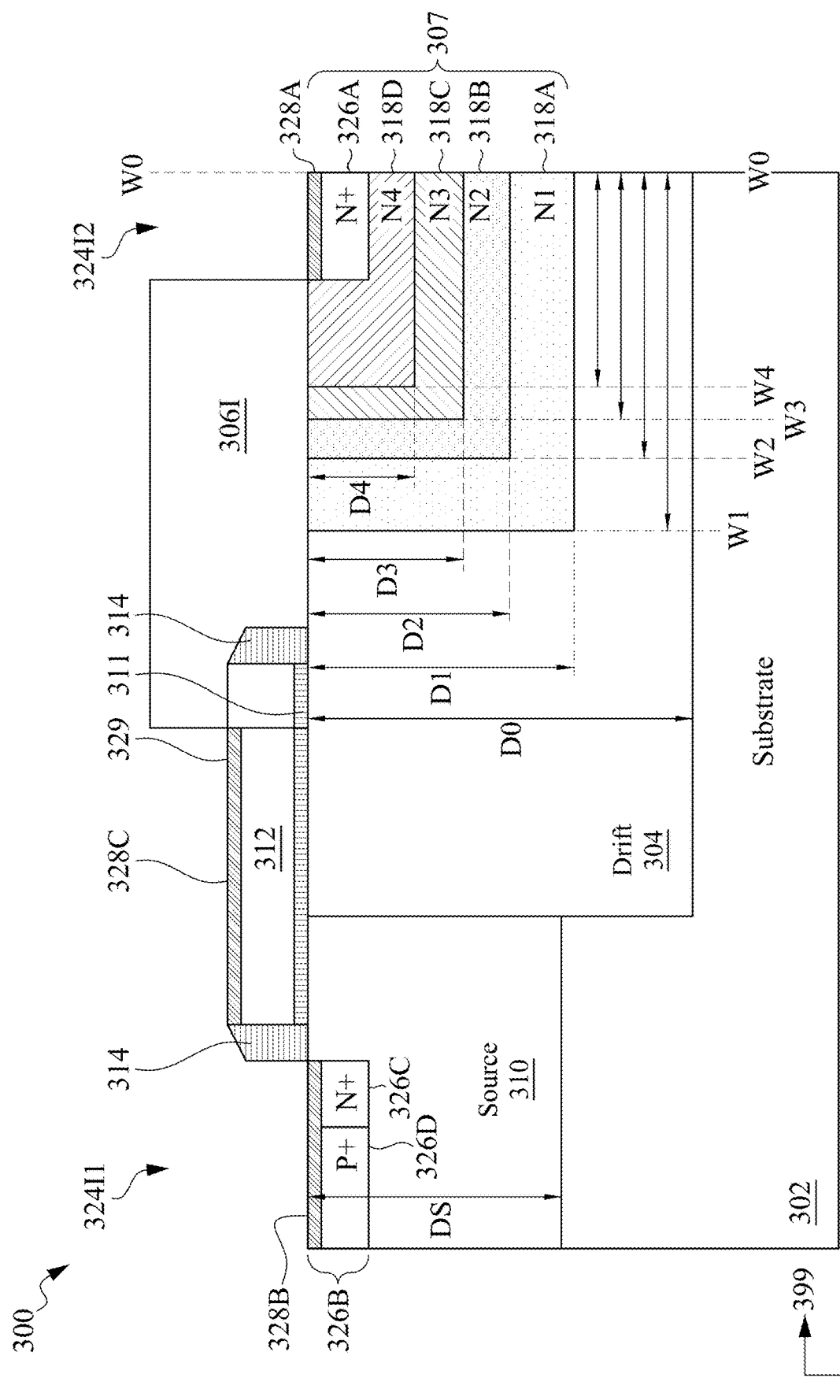

Method 200 includes an optional operation 212, wherein a silicide layer is formed on a top surface of the LDD regions and on top surface of the gate electrode. FIG. 3I is of an integrated circuit 300 after performance of steps associated with forming a silicide layer on the top surface of the LDD regions and the top surface of the gate electrode. Steps associated with forming a silicide layer include steps associated with: depositing a layer of patterning material over the substrate and the gate electrode, transferring a pattern to the layer of patterning material, and forming openings in the layer of patterning material. Further steps associated with forming the silicide layers include sputtering a thin metallic coating onto the top surface of the gate electrode, the source LDD region, and the drain LDD region of the LDMOS device, and annealing the LDMOS device in order to intermingle the thin metallic coating with the gate electrode material, with the source LDD region, and with the drain LDD region.

In some embodiments, the thin metallic coating is a layer of tungsten, cobalt, titanium, tantalum, platinum, palladium, or other metal suitable for forming silicide layers to electrically with contacts to a transistor in a semiconductor device. In some embodiments, the annealing process for the LDMOS device is a rapid laser anneal, to promote rapid heating and rapid cooling, restricting the degree of melting or inter-diffusion of metal atoms and the materials of the LDD regions. By reducing the amount of melting or inter-diffusion, the dopant distribution in the source LDD region and drain LDD region is preserved without spreading to the remainder of the source or drain wells of the LDMOS device.

FIG. 3I is a cross-sectional view of an integrated circuit 300 during a manufacturing process, in accordance with some embodiments. In FIG. 3I, layer of patterning material 306I is over the top surface of the drain well 307 and the drift region 304, the spacer 314 on the drain-well side of gate electrode material 312, and the top surface of the gate electrode material 312 closest to the drain well 307. Drain LDD silicide 328A is on a top surface of the drain LDD region 326A, source LDD silicide 328B is on the top surface of source LDD region 326B (both the source LDD zone 326C and the source LDD zone 326D), and gate electrode silicide 328C is on the top surface of gate electrode material 312 not covered by layer of patterning material 306I. Gate electrode silicide 328C is separated from spacer 314 on the drain-well side of the gate electrode material 312.

Figure 3J:
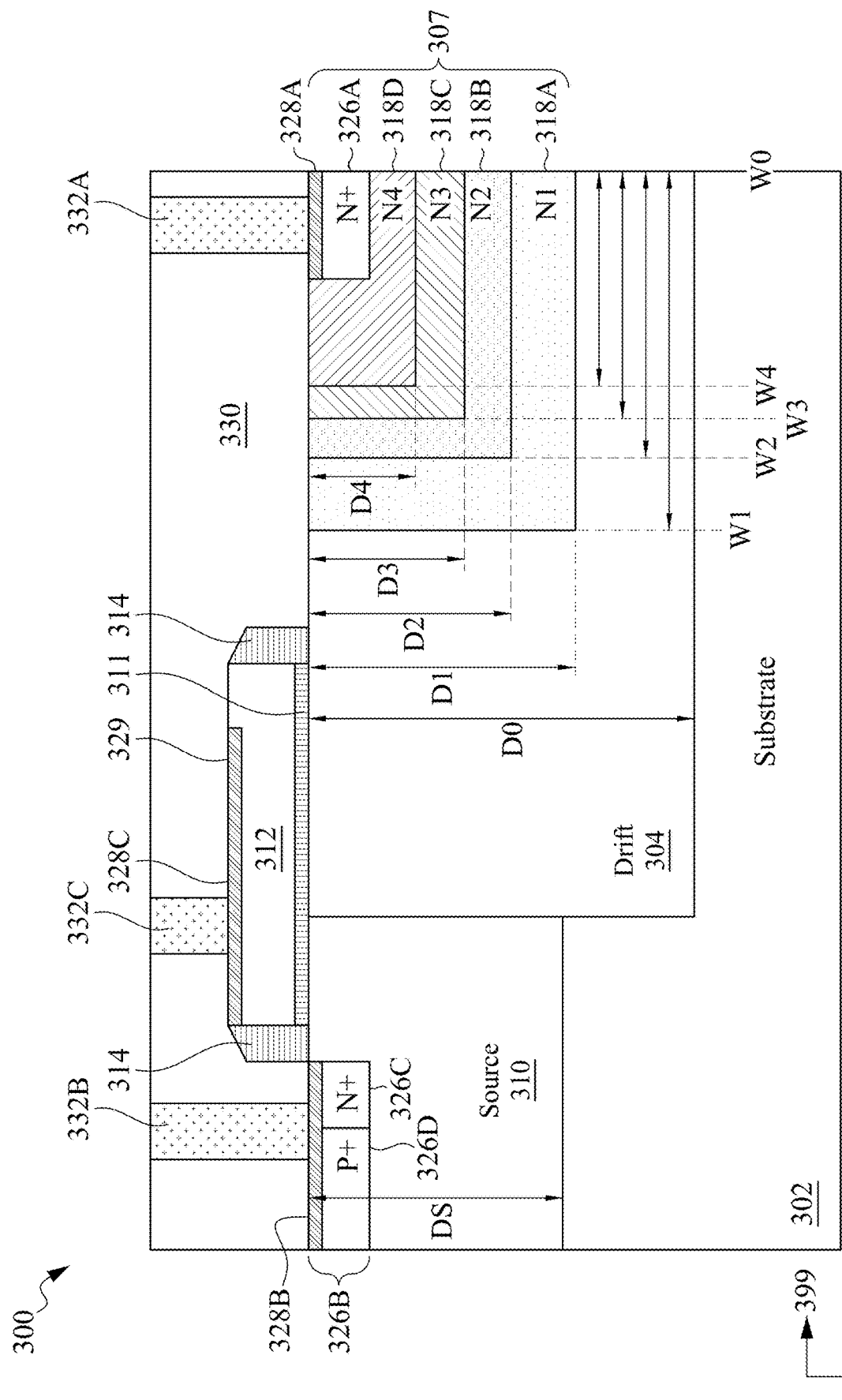

Method 200 includes an operation 214 wherein contacts are formed to the source well and to the drain well. FIG. 3J relates to an integrated circuit 300 after performing operation 214. In operation 214, a dielectric material (an inter layer dielectric, ILD) is deposited over the substrate, including the source well and the drain well, and the gate electrode. A layer of patterning material is deposited over the top surface of the ILD layer, a pattern transferred to the layer of patterning material, and openings are formed therein to expose the top surface of the ILD layer. An etch process is performed to form openings through the ILD layer exposing the source LDD silicide, the drain LDD silicide, and the gate electrode silicide. A metallic material (contact material) is deposited into the openings through the ILD layer to form electrical connections to the exposed silicide layers at the bottom of the ILD layer, and the LDMOS device is planarized with a chemical mechanical polishing process to expose the top surface of the ILD layer in preparation for other manufacturing steps in making the LDMOS device.

FIG. 3J is a cross-sectional view of an integrated circuit 300 during a manufacturing process, in accordance with some embodiments. In FIG. 3J, inter layer dielectric (ILD) layer 330 is deposited over the top surface of the drain well 307, the source well 310, and the gate electrode material 312. ILD layer 330 is a dielectric material such as silicon dioxide, BPSG, FSG, or some other insulating material suitable for electrically isolating elements of the LDMOS from each other in the semiconductor device.

Contacts 332A and 332B extend through ILD 330. Contact 332A extends through ILD 330 to electrically connect with drain LDD silicide 328A. Contact 332B extends through ILD 330 to electrically connect with source LDD silicide 328B. A gate electrode contact 332C extends through ILD 330 to electrically connect with gate electrode silicide 328C. Contacts are made of a conductive material such as tungsten, cobalt, titanium, platinum, palladium, or other metals or metal alloys which are compatible with LDMOS devices.

Figure 4A:
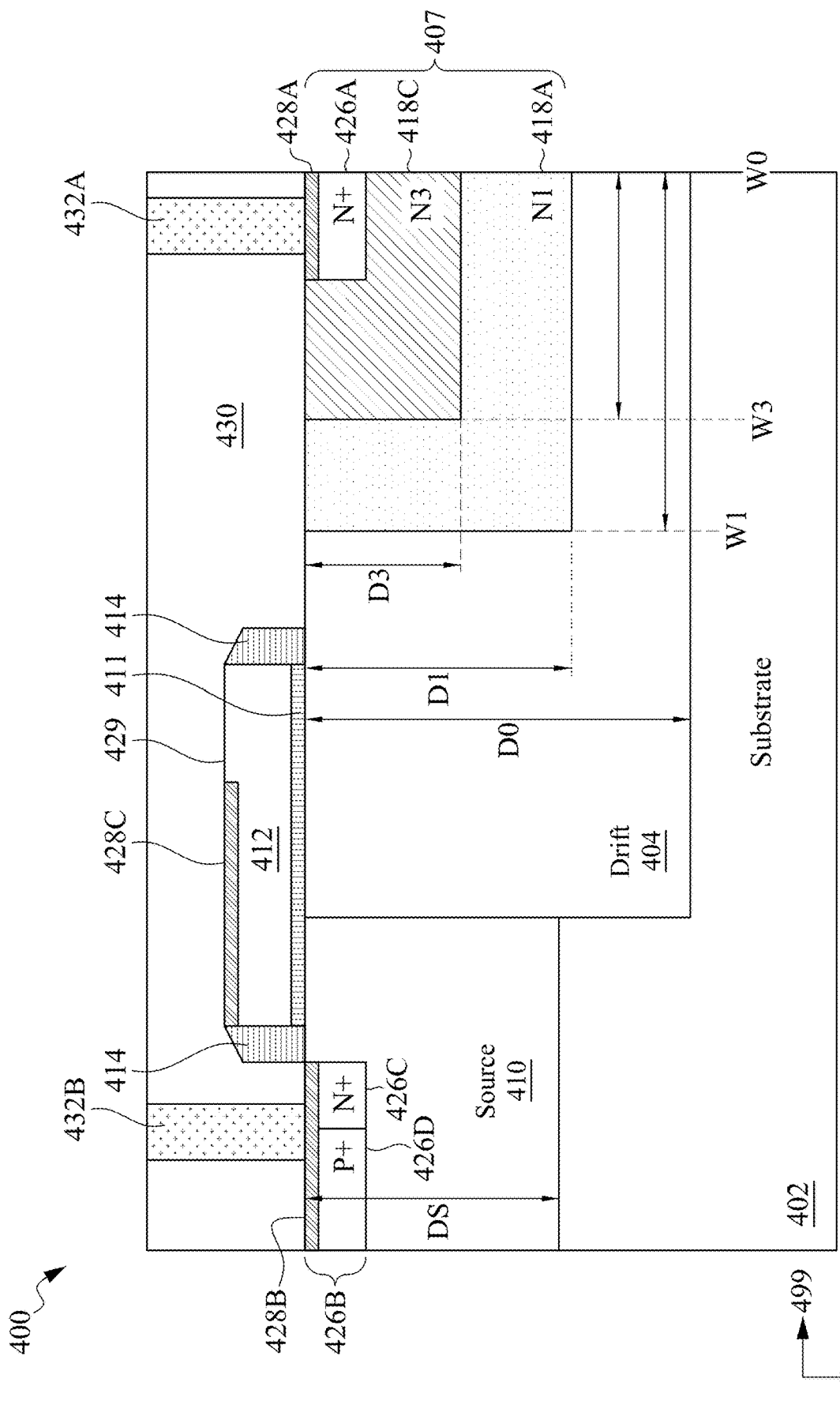
FIGS. 4A-4B are cross-sectional views of a LDMOS, in accordance with some embodiments.
Figure 4B:
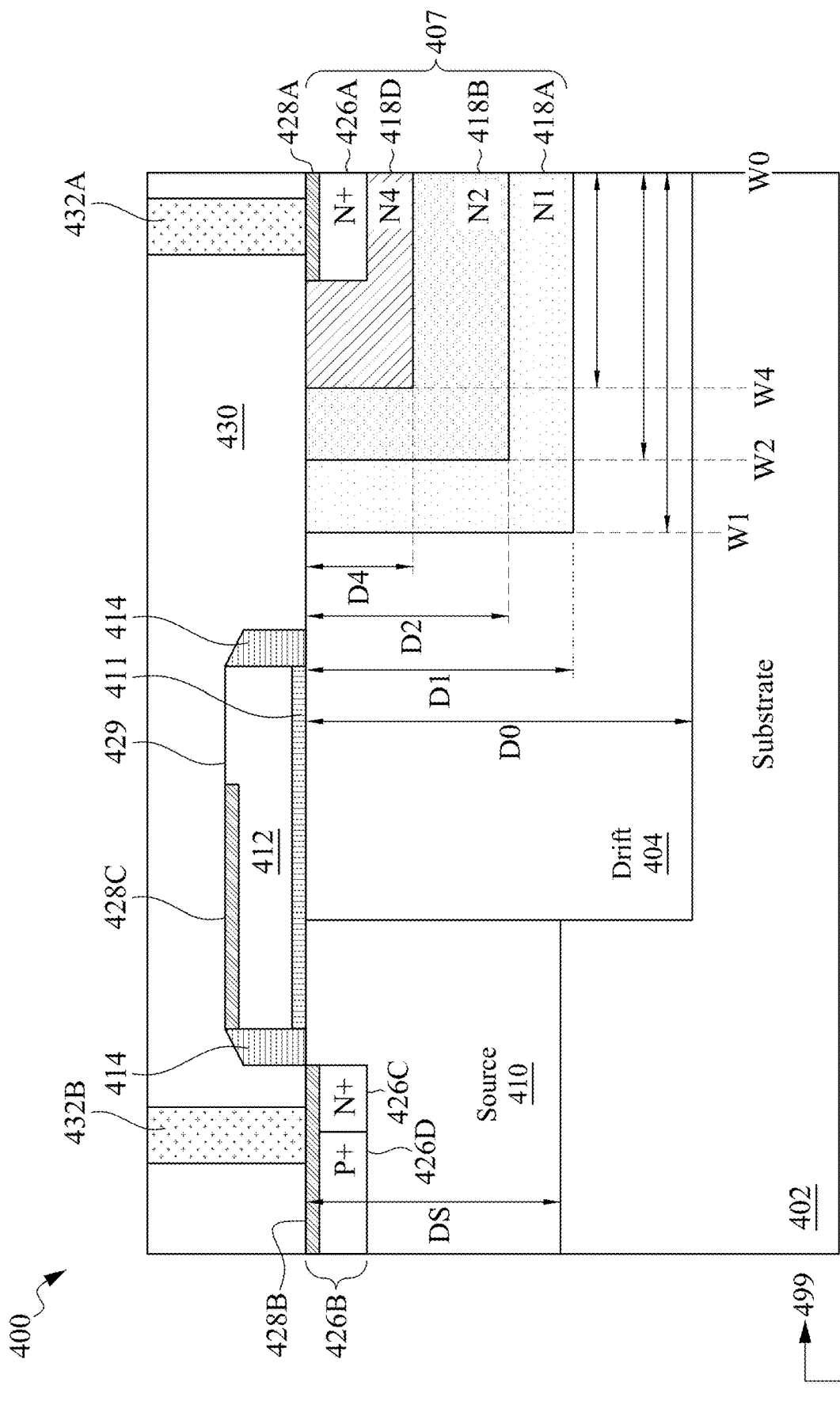

FIGS. 4A-4B are cross-sectional views of an integrated circuit 400, in accordance with some embodiments. FIG. 4A is a cross-sectional view of an integrated circuit 400 which includes two doped zones (N1 and N3) in the drain well 407, whereas in FIG. 3J the drain well 307 has four doped zones: N1, N2, N3, and N4. Elements of integrated circuit 400 which have a similar structure and/or function as the elements of integrated circuit 300, as described in FIG. 3J, have a same identifying numeral, incremented by 100.

In FIG. 4A, integrated circuit 400 includes an LDMOS device having a drain well 407 which comprises two doped zones, doped zone 418A and doped zone 418C, rather than the four doped zones (318A-318D) of integrated circuit 300, as described in FIG. 3J, above.

In FIG. 4A, doped zone 418A has a zone depth D1 and doped zone 418C has a zone depth D3, where D3<D1. Doped zone 418A has a zone width W1 and doped zone 418C has a zone width W3, where W3<W1. In some embodiments, the zone depths of the two doped zones are the same. Doped zone 418A has a smaller concentration of dopant atoms than the doped zone 418C, and a larger concentration of dopant atoms than the drift region 404.

In an embodiment of an LDMOS device with two doped zones, such as integrated circuit 400, the doped zones are made by two normal (0°) doping processes into the drain well with the same implant vector (e.g., two positive implant vectors, two normal (0°) implant vectors, or two negative implant vectors), with a spacer being added to the side of a mask layer between the first doping process to form the first doped zone, and the second doping process to form the second doped zone. Other methods of making an LDMOS with two doped zones are described further, below.

In FIG. 4B, integrated circuit 450 includes an LDMOS device having a drain well 407 which comprises three doped zones (e.g., N1, N2, and N4), doped zone 418A, doped zone 418B, and doped zone 418D, rather than the four dopes zones (318A-318D) of integrated circuit 300, as described in FIG. 3J, above. In an embodiment of an LDMOS device with three doped zones, the doped zones are made from three doping processes into the drain well. The doped zones are distinguished from each other by modifying the implant angle at which the doping process is performed, modifying the position of the edge of the doped zone (by, e.g., adding a spacer (see spacer 320, above) to the side of a mask, or combinations of implant angle modification and spacer addition). The doped zones are also distinguished from each other by the dopant concentrations therein, which result from modifying the implant dose for the doped zone, or modifying the implant time for the doping process. In FIG. 4B, doped zone 418A has a first dopant concentration which is smaller than the dopant concentration in doped zone 418B and the dopant concentration in doped zone 418D. Doped zone 418A has a zone depth D1 from the top surface of the substrate 402, which is larger than the zone depth D2 of the doped zone 418B, and the zone depth D4 of the doped zone 418D. Doped zone 418A has a zone width W1 which is larger than the zone width W2 of the doped zone 418B and the zone width W3 of the doped zone 418D.

FIGS. 5A-5C are cross-sectional views of an integrated circuit 500 during a manufacturing process, in accordance with some embodiments. In the cross sectional views of integrated FIG. 500, doped zones have combinations of non-vertical and vertical edges closest to the source 510 (see FIGS. 5A-5C, where N1 and N3 have angled vertical edges closest to the source 510, and where N2 and N4 have vertical edges closest to the source 510).

Elements of integrated circuit 500 in FIG. 5A which have a similar structure or function as elements of integrated circuit 300 in FIG. 3C have a same reference numeral, incremented by 200. Measurements which relate to a same structural feature have a same reference numeral without modification. In FIG. 5A, doped zone 518A has been formed in substrate 502 (or, in drift region 504), with a zone depth D1 which is smaller than the drift region depth D0.

Dopant atoms being added to doped zone 518A have an implant vector 508C which is at an implant angle 590C from reference line 589. Layer of mask material 516C protects the drift region in the shadow of the layer of the mask material 516C, preventing dopant atoms from being implanted into the implant shadow. Doped zone 518A has a lower zone width W1A and an upper zone width W1B, where W1B<W1A. A zone flare width F1 at the top of the doped zone is smaller than a zone flare width F2 at the bottom of the doped zone. Zone flare width F1 and Zone flare width F2 are measured form the edge of the doped zone 518A to a projection line extending down from the edge of the layer of mask material 516C on the top surface of the substrate 502. The edge of the doped zone below the layer of mask material 516C has an edge angle 591 which corresponds to the implant angle 590C with respect to the reference line 589. The absolute values of zone flare width F1 and zone flare width F2 are different with respect to each other because they are measured at different distances from the top surface of the substrate. However, F2 is always greater than F1 when implant angle 590C is negative (−), provided that zone flare width F2 is measured farther from the top surface of the substrate than zone flare width F1.

Elements of integrated circuit 500 in FIG. 5B which have a same structure or function as elements of integrated circuit 500 in FIG. 5A, as described above, have a same identifying numeral. Doped zone 518B is being formed by adding dopant atoms along implant vector 508D, which has a normal (0°) implant angle 590D with respect to the reference line 589. Doped zone 518B has a zone width W2 which is unchanging with respect to the depth of the edge of the doped zone from the top surface of the substrate 502. Doped zone 518A has a zone depth D1 which is larger than the zone depth D2 of doped zone 518B. Zone depth D1 is larger than zone depth D2, and both zone depth D1 and zone depth D2 are unchanging across drift region 504. In some embodiments, zone depth D1 is equal to zone depth D2. Doped zone 518A has a smaller dopant concentration than doped zone 518B.

In FIG. 5C, dopant atoms are being added to doped zone 518D along an implant vector 508F at an implant angle 590F from reference line 589. Implant angle 590F is a normal (0°) implant angle. Doped zone 518C separated doped zone 518B from doped zone 518D. Doped zone 518A and doped zone 518C have a same profile (e.g., due to a negative implant angle), and doped zone 518B and doped 518D have a same profile (e.g., due to a normal (0°) implant angle). Doped zone 518C has zone flare characteristics (e.g., wider at the bottom, narrower at the top) similar to the zone flare characteristics of doped zone 518A (where zone flare F1<zone flare F2, when zone flare F2 is measured deeper into substrate 502 than zone flare F1). Doped zones 518A-518D have dopant concentrations similar to the dopant concentrations described above for doped zones 318A-318D of integrated circuit 300.

In embodiments of LDMOS devices similar to integrated circuit 500, the zone flare at the top of the doped zones, for zones implanted at negative (−) implant angles, reduces to about zero (0) nanometer separation, and the doped zone having the smaller concentration (and the non-perpendicular zone edge). In some embodiments, the doped zones are separated from each other at the top surface by modifying the implant angle at which some doping processes are performed, or modifying the position of the edge of the doped zone (by, e.g., adding a spacer (see spacer 520) to the side of a mask material, or combinations of implant angle modification and spacer addition). Implant angles for doped zones of integrated circuit 500 are as follows: {−0−0}.

FIG. 5D is a cross-sectional view of an integrated circuit 501 during a manufacturing process, in accordance with some embodiments. In FIG. 5D, doped zones have alternating vertical and non-vertical edges closest to source 510 (e.g., doped zone 518A has a vertical edge closest to source 510, doped zone 518B has a non-vertical edge closest to source 510, doped zone 518C has a vertical edge closest to source 510, and doped zone 518D has a non-vertical edge closest to source 510). In integrated circuit 501, the doped zone 518A is formed by, e.g., a doping process which uses the top corner of the layer of mask material 516C, rather than the bottom corner of the layer of mask material (see layer of mask material 316C in FIG. 3D) to shield the substrate from implanted dopant atoms. For example, layer of mask material 516C extends to the inner edge of doped zone 518A, indicating that the implant angle for the dopant atoms added to form doped zone 518A had a normal implant vector (e.g., implant angle was 0°). The upper edge of doped zone 518B is offset away from the edge of layer of mask material 516C on the top surface of substrate 502. Adding dopant atoms to form doped zone 518B with a positive (+) implant angle takes advantage of the upper corner of layer of mask material 516C to shield the substrate in doped zone 518A, closest to the layer of mask material 516C, from the added dopant atoms. Thus, at the top surface, doped zones 518A and 518B are separated from each other across the top surface. Similarly, doped zone 518C aligns with an edge of spacer 520 and has an invariant width W3, indicating that the implant angle for doped zone 518C is about 0°. Doped zone 518D is separated from the spacer 520 on the top surface of substrate 502, indicating that the implant angle for doped zone 518D is a positive (+) implant angle. Implant angles for doped zones of integrated circuit 503 are as follows: {0+0+}.

FIG. 5E is a cross-sectional view of an integrated circuit 503 during a manufacturing process, in accordance with some embodiments. In FIG. 5E, all of the doped zones of integrated circuit 503 have non-vertical edges closest to source 510. The drain well 507 of integrated circuit 503 differs from the drain well of integrated circuit 501, as follows. In FIG. 5E, doped zone 518A has been formed with a negative implant angle, doped zone 518B has been formed with a positive implant angle, doped zone 518C has been formed with a negative implant angle, and doped zone 518D is being formed with a positive implant angle. Thus, implant angles for doped zones of integrated circuit 503 are as follows: {−+−+}. Doped zone 518A has a zone depth D1, doped zone 518B has a zone depth D2, doped zone 518C has a zone depth D3, and doped zone 518D ahs a zone depth D4, where D4<D3<D2<D1. Doped zone 518A has a lower zone width W1A and an upper zone width W1B, where W1A>W1B. Doped zone 518B has a lower zone width W2A and an upper zone width W2B, where W2A>W2B. Doped zone 518C has a lower zone width W3A and an upper zone width W3B, where W3A>W3B. Doped zone 518D has a lower zone width W4A and an upper zone width W4B, where W4A>W4B. Further, W1A>W1B>W2A>W2B>W3A>W3B>W4A>W4B. Thus, at the top surface of the substrate 502, each doped zone is separated from the edge of the adjacent doped zones to further increase the ability of the drain well to avoid succumbing to the Kirk effect (base pushout) during high-current operation.

Figure 6:
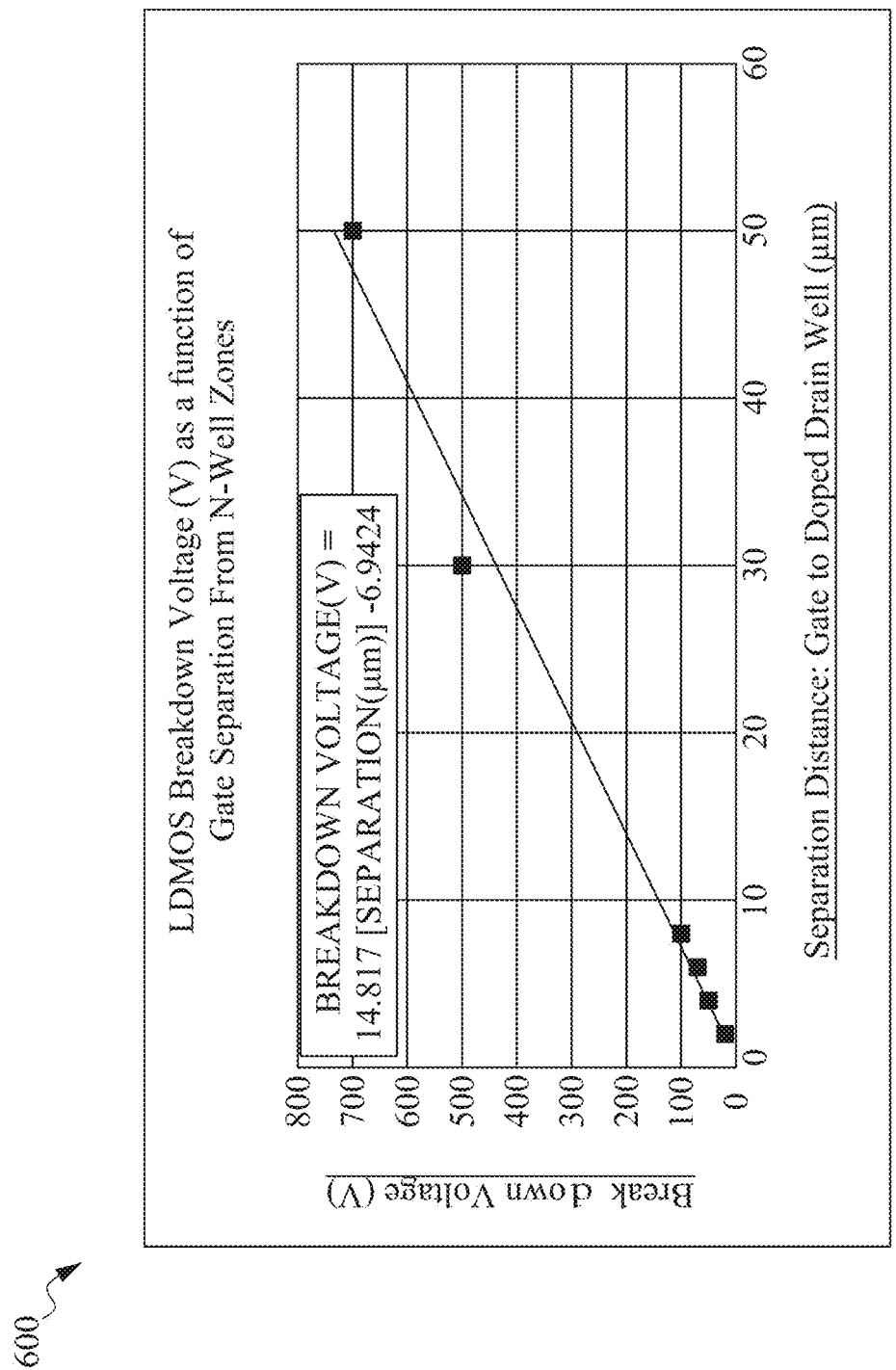
FIG. 6 is a chart of breakdown voltages for a LDMOS device, in accordance with some embodiments.

FIG. 6 is a chart 600 of breakdown voltages for LDMOS devices according to the data provided above regarding the separation distance (μm) between gate electrode and the drain well, and the associated breakdown voltage (V) for the above-provided separation distances. The breakdown voltage of an LDMOS device is a function of the separation distance between the edge of the gate electrode closest to the drain well and the edge of the doped zone in the drain well with the second-lowest dopant concentration therein closest to the gate electrode. In a non-limiting example, separation distance 129 in integrated circuit 100 is the distance between the top edge of the doped zone 118A and the closest edge of the gate electrode 112. The breakdown voltage for an LDMOS device increases by approximately 14 volts (V) per micrometer (μm) of distance between the edge of the gate electrode closest to the drain well (see drain well 107 in FIG. 1A, above) and the inner edge of the second doped zone of the drain well (see doped zone 118A of drain well 107 in FIG. 1A, above).

In some embodiments, an LDMOS device with a separation distance of 1-3 μm between the gate electrode and the drain well has a breakdown voltage of about 20 Volts. In some embodiments, an LDMOS device with a separation distance of 3-5 μm between the gate electrode and the drain well has a breakdown voltage of about 50 Volts. In some embodiments, an LDMOS device with a separation distance of 5-7 μm between the gate electrode and the drain well has a breakdown voltage of about 70 Volts. In some embodiments, an LDMOS device with a separation distance of 7-9 μm between the gate electrode and the drain well has a breakdown voltage of about 100 Volts. In some embodiments, an LDMOS device with a separation distance of 20-40 μm between the gate electrode and the drain well has a breakdown voltage of about 500 Volts. In some embodiments, the breakdown voltage is about 1200 V. In some embodiments, an LDMOS device with a separation distance of 40-60 μm between the gate electrode and the drain well has a breakdown voltage of about 700 Volts. Thus, a correlation between breakdown voltage and separation distance between the gate electrode and the drain well is about 14.8 V/μm.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes an integrated circuit. The integrated circuit also includes a drift region in a substrate; a drain in the substrate, where the drain may include a doped drain well, where the doped drain well may include: a first zone, where the first zone has a first concentration of a first dopant; and a second zone, where the second zone has a second concentration of the first dopant, and the first concentration is less than the second concentration; and a gate electrode over the drift region, the gate electrode being separated from the doped drain well in a direction parallel to a top surface of the substrate by a distance greater than 0. Other embodiments of this aspect include corresponding computer systems, apparatus, and computer programs recorded on one or more computer storage devices, each configured to perform the actions of the methods.

Implementations may include one or more of the following features. The integrated circuit where the drift region has a third concentration of the first dopant, and the third concentration is less than the first concentration. The second zone is separated from the drift region by the first zone. The drain further may include a drain low-density doped (LDD) region, and the first zone of the doped drain well is separated from the drain LDD region by the second zone. The third zone separates the second zone from the drain LDD region and has a third concentration of the first dopant larger than the second concentration of the first dopant in the second zone. The fourth zone separates the third zone form the drain LDD region, the fourth zone having a fourth concentration of the first dopant larger than the third concentration of the first dopant in the third zone. The first zone has a first depth below a top surface of the substrate, the second zone has a second depth below the top surface of the substrate, and the first depth is different from the second depth. The first zone has a first depth below a top surface of the substrate, and the second zone has the first depth below the top surface of the substrate. The first zone has a first width between the second zone and the drift region at a top surface of the substrate, and a second width between the second zone and the drift region at a bottom of the drift region, where the first width and the second width are different widths measured in a direction parallel to the top surface of the substrate. The integrated circuit may include: a gate electrode over the top surface of the substrate; and an electrode silicide layer extending across less than an entirety of a top surface of the gate electrode. Implementations of the described techniques may include hardware, a method or process, or computer software on a computer-accessible medium.

One general aspect includes a method of making an integrated circuit. The method of making also includes forming a drift region in a substrate, the drift region having a first dopant type; forming a drain well in the drift region, the drain well having the first dopant type, the drain well may include a first zone with a first concentration of the first dopant and a second zone having a second concentration of the first dopant different from the first concentration of the first dopant; forming a source well in the substrate, the source well having a second dopant type opposite from the first dopant type, the source well being adjacent to the drift region in the substrate; forming a gate electrode over a top surface of the substrate over the drift region and the source well, and being laterally separated from the drain well; forming a drain low-density doped (LDD) region in the second zone of the drain well. Other embodiments of this aspect include corresponding computer systems, apparatus, and computer programs recorded on one or more computer storage devices, each configured to perform the actions of the methods.

Implementations may include one or more of the following features. The method where forming a drain well in the drift region further may include: depositing a spacer on sides of the gate electrode; depositing a mask layer over the gate electrode and the substrate; forming an opening in the mask layer exposing the drift region; forming the first zone by implanting dopants of the first dopant type at a first implant angle into the drift region; Forming a drain well in the drift region further may include: forming the second zone by implanting dopants of the first dopant type at a second implant angle into the first zone, where the first implant angle is different from the second implant angle. The method may include forming a silicide layer on a top surface of the source LDD region, the drain LDD region, and an exposed portion of the gate electrode. Forming the first zone further may include implanting dopants of the first dopant type at the first implant angle to a first depth, and forming the second zone further may include implanting dopants of the first dopant type into the first zone at the second implant angle to the first depth. The method may include: forming a second spacer on a side of the mask layer over the drift region; forming a third zone in the substrate by implanting dopants of the first dopant type into the second zone at a third implant angle to a third depth; and forming the drain LDD region in the third zone. The fourth implant angle is smaller than the third implant angle; and forming the drain LDD region in the fourth zone. Implementations of the described techniques may include hardware, a method or process, or computer software on a computer-accessible medium.

One general aspect includes a device. The device also includes a source well in a substrate; a drift region in the substrate; a drain well in the substrate, the drain well may include a drain LDD region, and separated from the source well by the drift region, where the drain LDD region, the drift region is adjacent to the source well and separating the source well from the drain well, and where the drain well may include a first zone and a second zone, the first zone having a first concentration of a first dopant, the second zone having a second concentration of the first dopant; and a first width of the first zone between the drift region and the second zone at the top surface of the substrate is smaller than a second width of the first zone between the drift region and the second zone at the bottom of the second zone. The device also includes a gate electrode over the source well and the drift region, the gate electrode being laterally separated from the drain well at the top surface of the substrate. Other embodiments of this aspect include corresponding computer systems, apparatus, and computer programs recorded on one or more computer storage devices, each configured to perform the actions of the methods.

Implementations may include one or more of the following features. The device where the drain LDD region has a third concentration of the first dopant; the first concentration of the first dopant being smaller than the second concentration of the first dopant; and the second concentration of the first dopant being smaller than the third concentration of the first dopant. The drift region has a fourth concentration of the first dopant smaller than the first concentration of the first dopant in the first zone. Implementations of the described techniques may include hardware, a method or process, or computer software on a computer-accessible medium.

It will be readily seen by one of ordinary skill in the art that one or more of the disclosed embodiments fulfill one or more of the advantages set forth above. After reading the foregoing specification, one of ordinary skill will be able to affect various changes, substitutions of equivalents and various other embodiments as broadly disclosed herein. It is therefore intended that the protection granted hereon be limited only by the definition contained in the appended claims and equivalents thereof.

What is claimed is:

1. An integrated circuit, comprising:
   a drift region in a substrate;
   a drain in the substrate, wherein the drain comprising a doped drain well, wherein the doped drain well comprises:
      a first zone, wherein the first zone has a first concentration of a first dopant; and
      a second zone, wherein the second zone has a second concentration of the first dopant, a top-most surface of the first zone is coplanar with a top-most surface of the second zone, and the first concentration is less than the second concentration; and
   a gate electrode over the drift region, the gate electrode being separated from the doped drain well in a direction parallel to a top surface of the substrate by a distance greater than 0.

2. The integrated circuit of claim 1, wherein the drift region has a third concentration of the first dopant, and the third concentration is less than the first concentration.

3. The integrated circuit of claim 1, wherein the second zone is separated from the drift region by the first zone.

4. The integrated circuit of claim 1, wherein the drain further comprises a drain low-density doped (LDD) region, and the first zone of the doped drain well is separated from the drain LDD region by the second zone.

5. The integrated circuit of claim 4, further comprising a third zone, wherein the third zone separates the second zone from the drain LDD region and has a third concentration of the first dopant larger than the second concentration of the first dopant in the second zone.

6. The integrated circuit of claim 5, further comprising a fourth zone, wherein the fourth zone separates the third zone form the drain LDD region, the fourth zone having a fourth concentration of the first dopant larger than the third concentration of the first dopant in the third zone.

7. The integrated circuit of claim 1, wherein the first zone has a first depth below a top surface of the substrate, the second zone has a second depth below the top surface of the substrate, and the first depth is different from the second depth.

8. The integrated circuit of claim 1, wherein an entire sidewall of the first zone is at an acute angle with respect to the top surface of the substrate.

9. The integrated circuit of claim 1, wherein the first zone has a first width between the second zone and the drift region at a top surface of the substrate, and a second width between the second zone and the drift region at a bottom of the drift region, wherein the first width and the second width are different widths measured in a direction parallel to the top surface of the substrate.

10. The integrated circuit of claim 1, further comprising:
    the gate electrode over the top surface of the substrate; and
    an electrode silicide layer extending across less than an entirety of a top surface of the gate electrode.

11. A device, comprising
    a source well in a substrate;
    a drift region in the substrate;
    a drain well in the substrate, the drain well comprising a drain LDD region, and separated from the source well by the drift region, wherein
       the drain well comprises a first zone and a second zone, the first zone having a first concentration of a first dopant, the second zone having a second concentration of the first dopant, a top-most surface of the first zone is coplanar with a top-most surface of the drain LDD region; and a first width of the first zone between the drift region and the second zone at the top surface of the substrate is smaller than a second width of the first zone between the drift region and the second zone at the bottom of the second zone; and
    a gate electrode over the source well and the drift region, the gate electrode being laterally separated from the drain well at the top surface of the substrate.

12. The device of claim 11, wherein
    the drain LDD region has a third concentration of the first dopant;

the first concentration of the first dopant being smaller than the second concentration of the first dopant; and the second concentration of the first dopant being smaller than the third concentration of the first dopant.

13. The device of claim 11, wherein the drift region has a fourth concentration of the first dopant smaller than the first concentration of the first dopant in the first zone.

14. A semiconductor device, comprising:
a drift region in a substrate;
a source in the substrate, wherein the source is in direct contact with the drift region;
a drain in the drift region, wherein the drain comprises:
   a first zone, wherein the first zone has a first concentration of a first dopant; and
   a second zone, wherein the second zone has a second concentration of the first dopant, and the first concentration is less than the second concentration; and
a gate structure overlapping the source and the drift region, wherein an entirety of the drain is spaced from the gate structure in a direction parallel to a top surface of the substrate.

15. The semiconductor device of claim 14, wherein the first zone directly contacts a bottom surface and a sidewall of the second zone.

16. The semiconductor device of claim 14, wherein the drain further comprises a third zone, wherein the third zone has a third concentration of the first dopant, and the third concentration is greater than the second concentration.

17. The semiconductor device of claim 16, wherein the drain further comprises a fourth zone, wherein the fourth zone has a fourth concentration of the first dopant, and the fourth concentration is greater than the third concentration.

18. The semiconductor device of claim 17, wherein the drain further comprises a lightly doped drain (LDD) region in contact with the fourth zone.

19. The semiconductor device of claim 14, wherein a depth of the first zone is greater than a depth of the second zone.

20. The semiconductor device of claim 14, wherein a width of the first zone in the direction is greater than a width of the second zone in the first direction.

* * * * *